US005788099A

United States Patent [19]
Treu et al.

[11] Patent Number: 5,788,099
[45] Date of Patent: Aug. 4, 1998

[54] VESSEL FOR CONTAINING BATCH QUANTITIES OF DIALYSATE OR OTHER PHYSIOLOGIC SOLUTION CHEMICALS

[75] Inventors: Dennis M. Treu, Gurnee; Dilip H. Shah, Grayslake; Donald C. Walker, Mundelein; Kenneth E. Pawlak, Vernon Hills, all of Ill.

[73] Assignee: AKYSYS, Ltd., Lincolnshire, Ill.

[21] Appl. No.: 660,694

[22] Filed: Jun. 5, 1996

Related U.S. Application Data

[63] Continuation-in-part of Ser. No. 388,275, Feb. 13, 1995, Pat. No. 5,591,344.

[51] Int. Cl.⁶ .................................................. B65D 39/00
[52] U.S. Cl. .......................... 215/230; 215/301; 215/302; 215/330; 215/DIG. 3; 220/254; 220/258; 220/277; 141/329; 141/330; 222/81; 222/83; 222/541.2
[58] Field of Search .................................. 215/230, 301, 215/302, 330, DIG. 3; 220/254, 258, 277; 141/329, 330; 222/81, 83, 541.2

[56] References Cited

U.S. PATENT DOCUMENTS

| | | |
|---|---|---|
| 710,219 | 9/1902 | Snow . |
| 1,170,152 | 2/1916 | Heath . |
| 1,773,553 | 8/1930 | Taylor et al. . |
| 2,723,060 | 11/1955 | Rieke ........................ 222/541.2 X |
| 3,207,375 | 9/1965 | Bereziat et al. ............. 222/541.2 X |
| 3,425,598 | 2/1969 | Kobernick ................... 222/541.2 X |
| 3,871,545 | 3/1975 | Bereziat ......................... 215/330 X |
| 4,126,244 | 11/1978 | Elser . |
| 4,197,942 | 4/1980 | Gacki et al. . |
| 4,247,001 | 1/1981 | Wiegner . |
| 4,303,067 | 12/1981 | Connolly et al. ............. 215/247 X |
| 4,426,019 | 1/1984 | Sedam . |
| 4,646,926 | 3/1987 | Agbay et al. .................... 215/203 |
| 4,724,977 | 2/1988 | Cleevely et al. ................. 220/258 |
| 4,760,941 | 8/1988 | Salmon et al. ................... 222/153 |
| 4,903,865 | 2/1990 | Janowitz .................... 222/541.2 X |
| 5,388,690 | 2/1995 | Mutterle et al. ................. 206/222 |
| 5,482,176 | 1/1996 | Maietta et al. . |
| 5,547,645 | 8/1996 | Ego et al. . |

*Primary Examiner*—Stephen Cronin
*Attorney, Agent, or Firm*—McDonnell Boehnen Hulbert & Berghoff

[57] ABSTRACT

A vessel for containing a batch quantity of chemicals for preparation of physiologic, therapeutic, or irrigation solutions, such as dialysate. The vessel has a cap and a bottle shell having features that make the vessel suitable for mounting to an apparatus for automatically opening the vessel. In a preferred embodiment, the cap has a frangible membrane sealing the vessel. A protective overcap is removably mounted to the cap to protect the cap from puncture prior to installation on the opening apparatus.

9 Claims, 20 Drawing Sheets

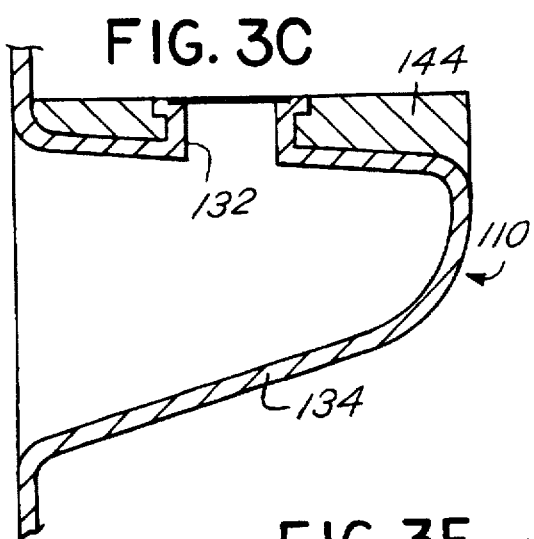
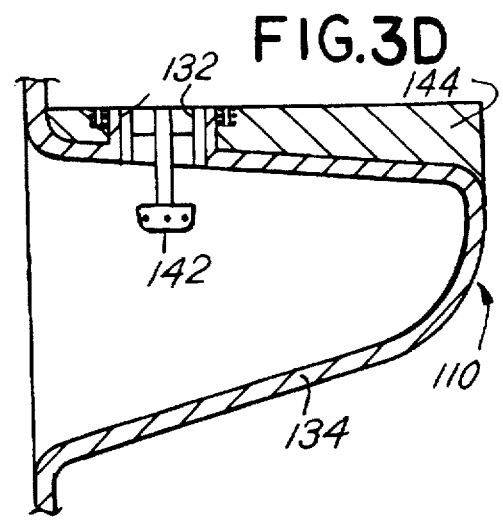
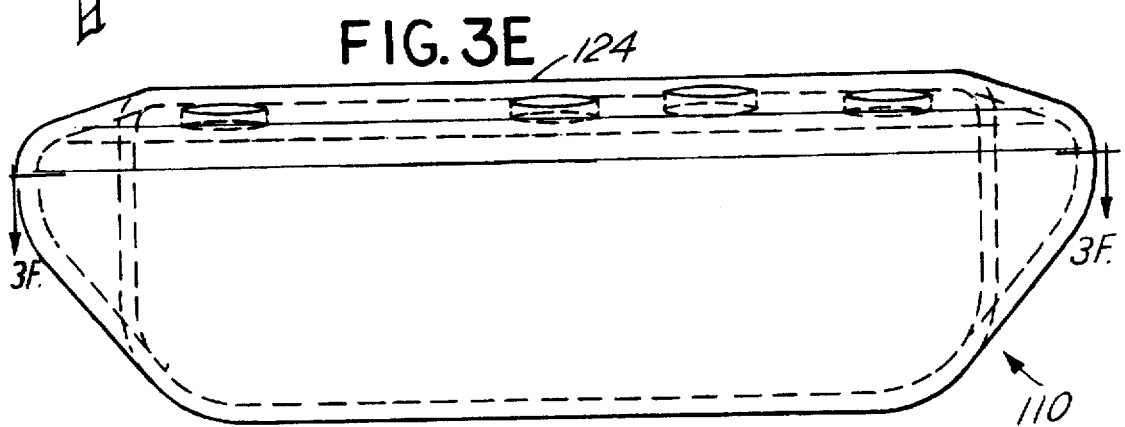
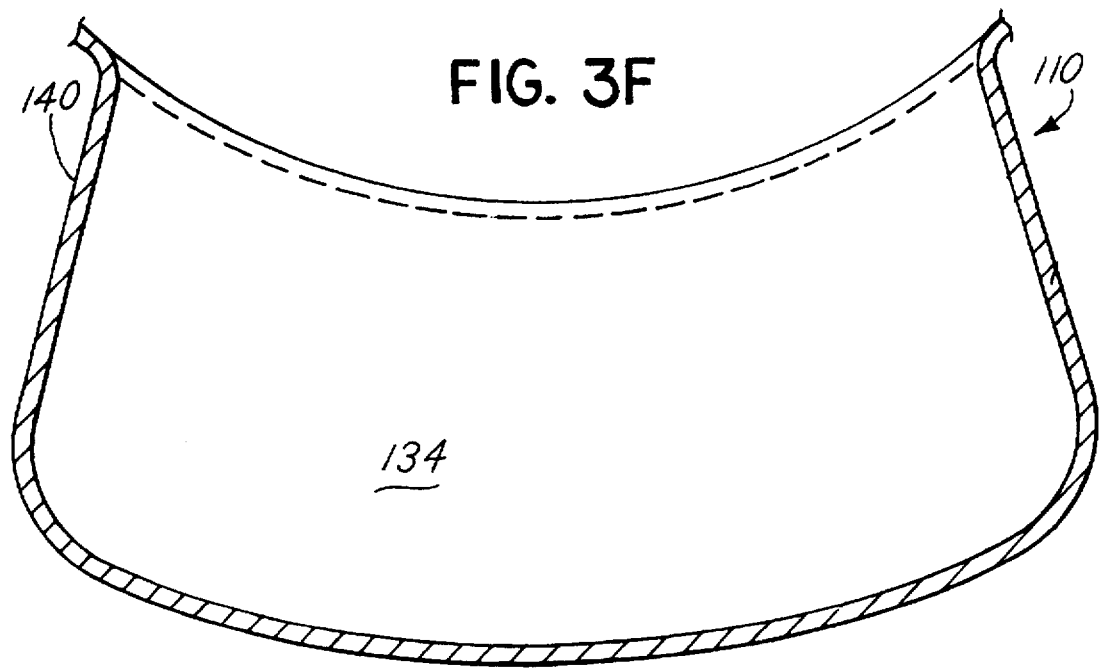

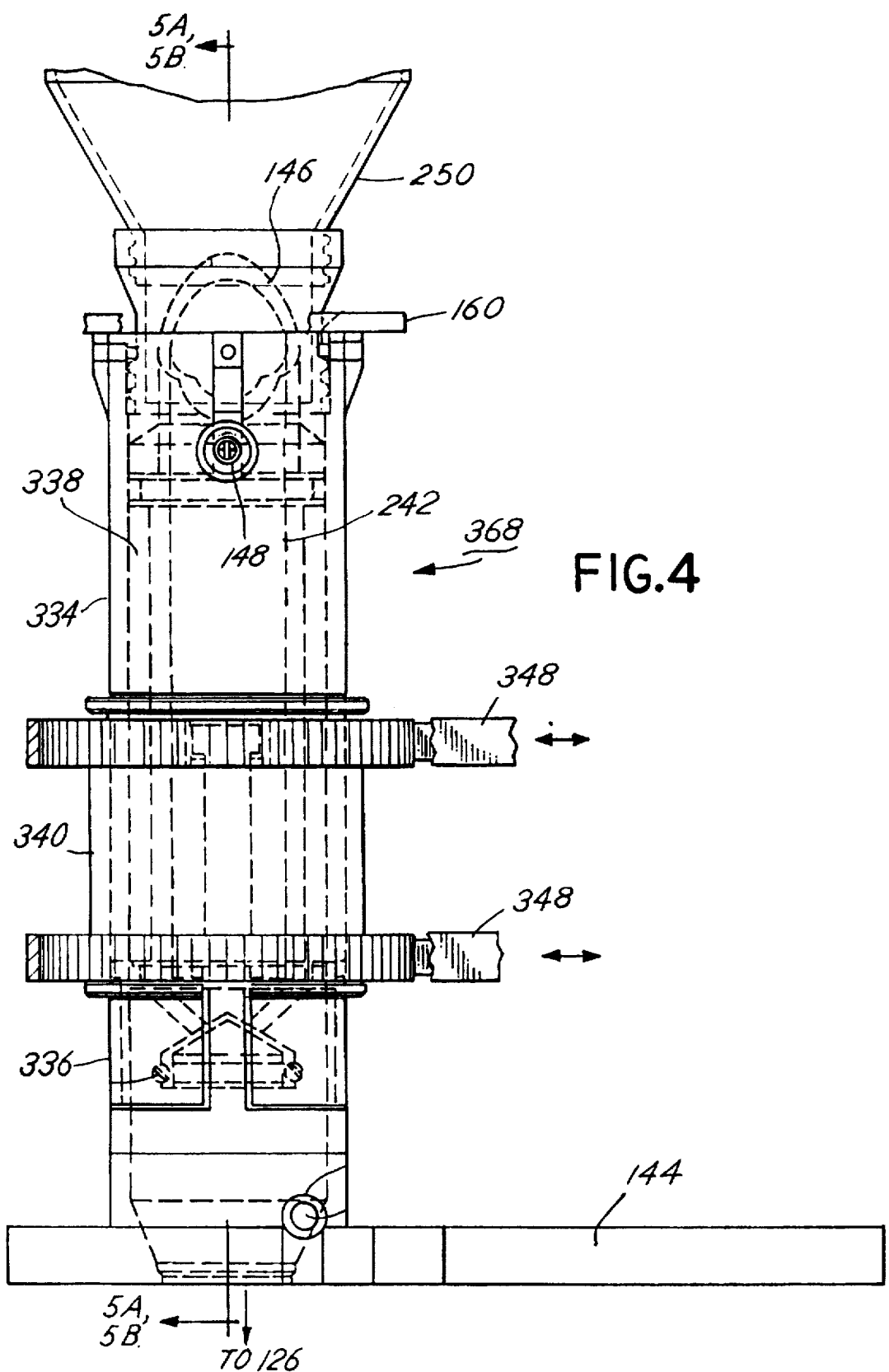

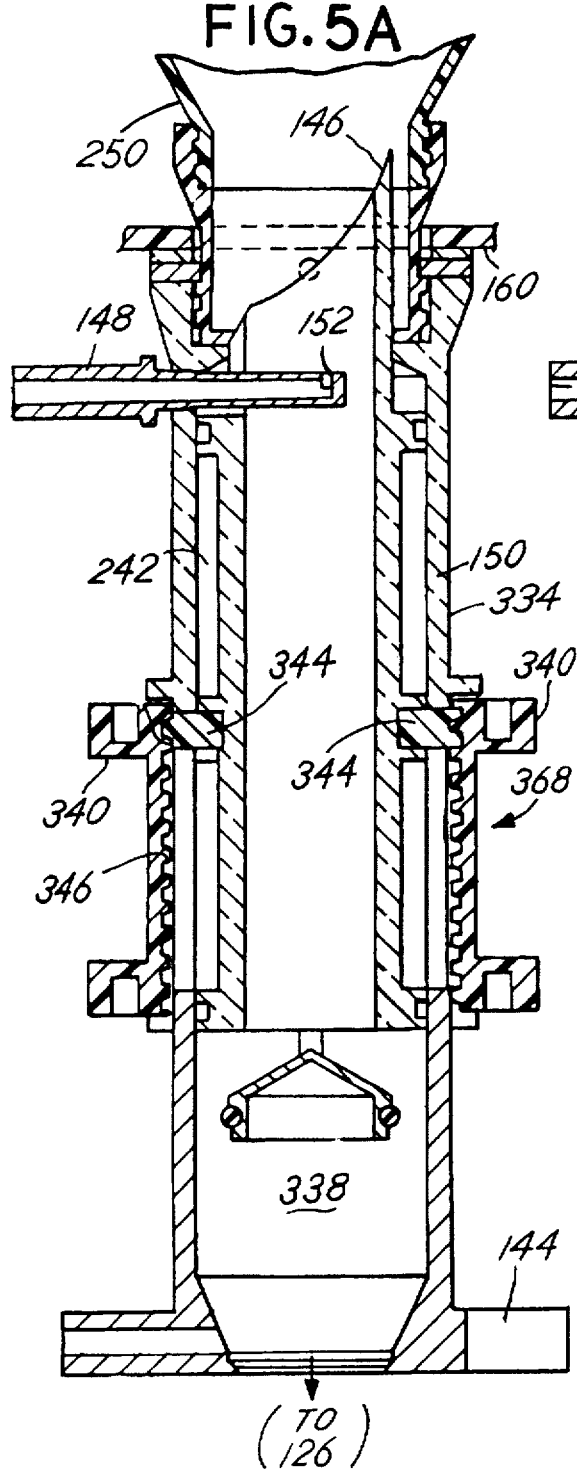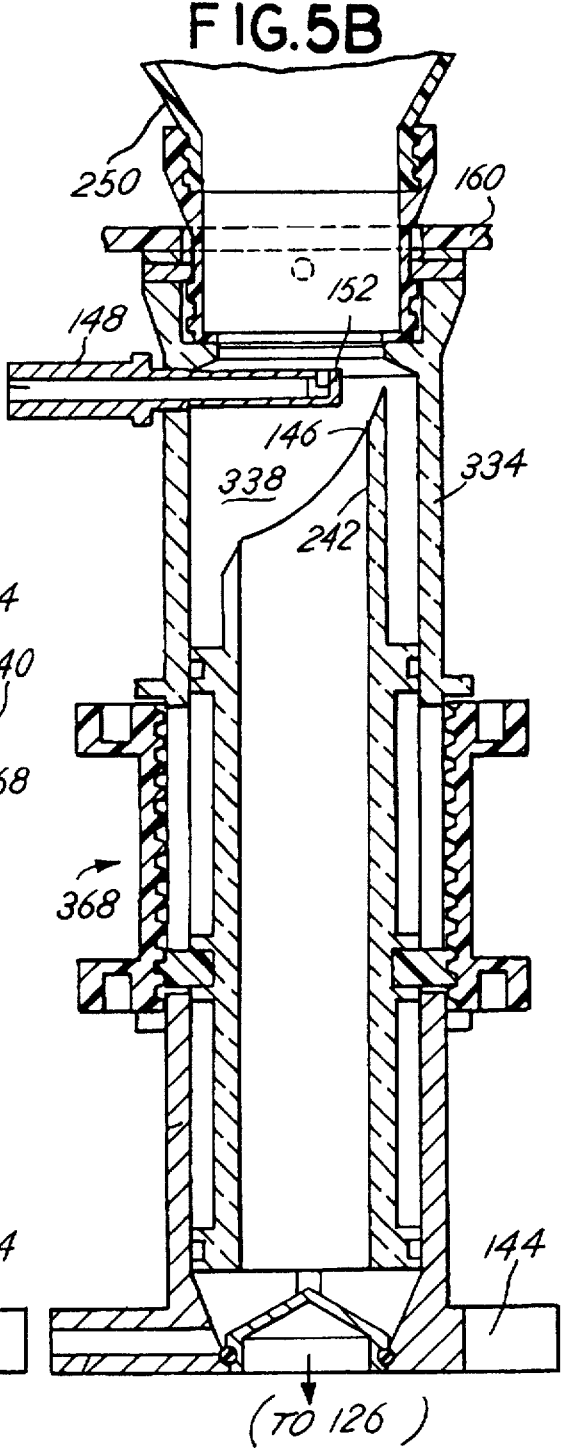

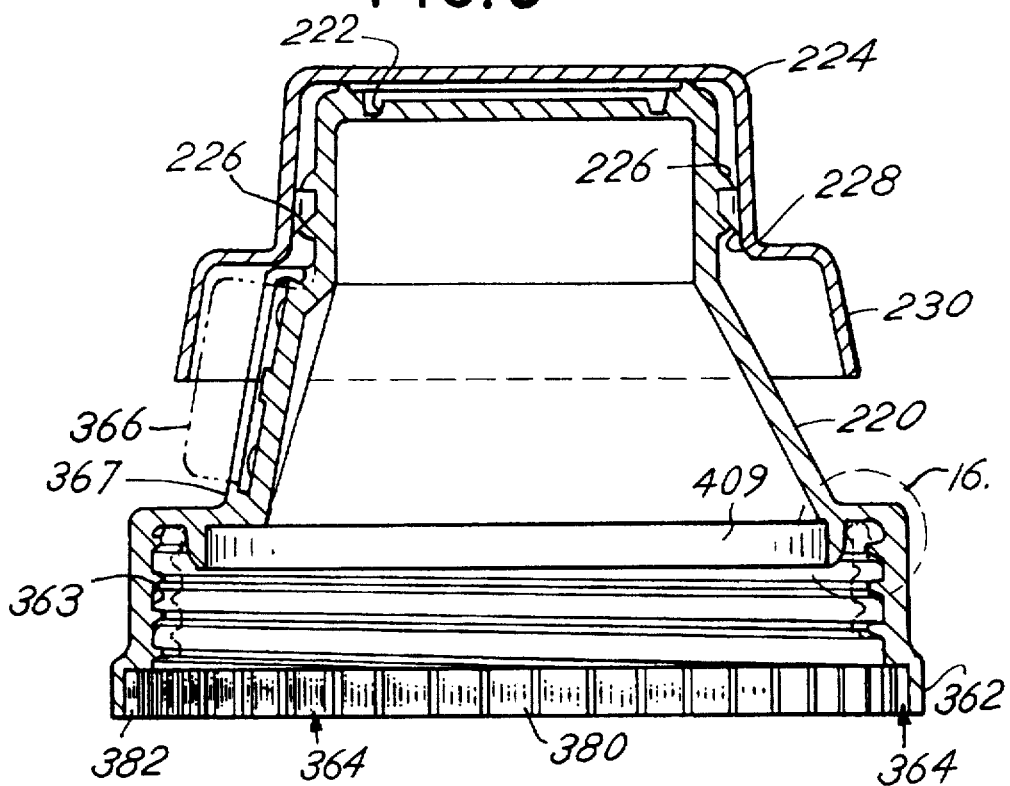
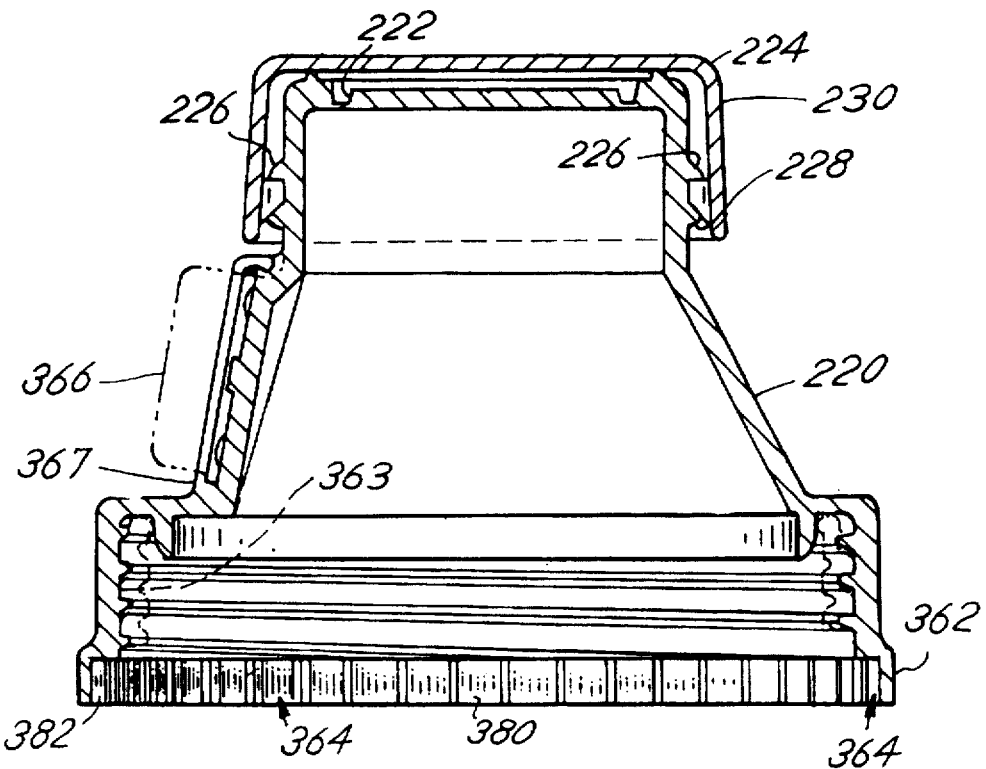

VESSEL FOR CONTAINING BATCH QUANTITIES OF DIALYSATE OR OTHER PHYSIOLOGIC SOLUTION CHEMICALS

RELATED APPLICATION

This is a Continuation-In-Part of prior application Ser. No. 08/388,275 filed Feb. 13, 1995, now U.S. Pat. No. 5,591,344, the entire content of which is incorporated by reference herein.

FIELD OF THE INVENTION

The invention relates to vessels or bottles for containing chemicals for preparation of physiologic, therapeutic, or irrigation fluids, and more particularly to vessels for containing batch quantities of such chemicals. The inventive bottles are preferably used in conjunction with a machine that automatically releases the contents of the vessels into a suitable solution tank, such as a dialysis machine.

BACKGROUND OF THE INVENTION

Dialysis, including hemodialysis and peritoneal dialysis, is a treatment for patients that suffer from inadequate kidney function. In hemodialysis, blood is pumped from the patient's body through an extracorporeal artificial kidney circuit, where blood-borne toxins and excess water are filtered out of the blood through a semipermeable dialyzer membrane into an electrolyte (dialysate) medium. In the prior art, the dialysate solution has been typically prepared continuously on-line by combining water, which has been first purified by a separate water treatment system, with liquid concentrates of electrolytes using a proportioning pump. A representative patent discussing this technique is the patent to Serfass, U.S. Pat. No. 3,441,135.

The present invention is applicable to machines that prepare the physiologic or therapeutic solution a batch at a time. The invention specifically provides for vessels that are suitable for storing batch quantities of the dialysate or other solution chemicals, and suitable for automatic release of the chemicals from the vessels into a dialysate preparation tank. The dialysate is prepared in batch quantities, e.g., 50 liters, which is sufficient for one complete dialysis session. After the end of the session, the tank is cleaned, the empty vessel is removed, and a new vessel is installed on the dialysis machine for the next treatment. The vessels and the machine may be used to prepare other types of physiologic and therapeutic solutions for delivery to the patient, such as peritoneal dialysate, as well as irrigation fluids for use in surgery, e.g., arthroscopic surgery or transurethral resection. A complete discussion of a machine suitable for preparation of the physiologic or therapeutic solutions for use with the subject vessels is found in the prior Kenley et al. patent application Ser. No. 08/388,275 filed Feb. 13, 1995, incorporated by reference herein.

Ideally, the bottle for this particular use has to be tamper resistant, capable of adapting to the opening apparatus and being opened automatically, capable of withstanding extremes of temperature, and contain some capability of automatically identifying the contents of the vessel so as to insure that the correct chemicals are being introduced into the tank. Our vessel has a number of useful features that make the vessel ideally suitable to storing batch quantities of chemicals for automatic introduction into a batch preparation tank. The present inventors are unaware of any prior art vessels or bottles which are suitable for this purpose.

SUMMARY OF THE INVENTION

The present invention is a vessel, mountable to an apparatus for opening the vessel, containing a batch quantity of chemicals for preparation of physiologic, therapeutic, or irrigation fluids. In the preferred embodiment, the vessel is used for dialysate chemicals. The vessel has a bottle shell having a neck portion and a cap threadably engaging with the neck portion and covering the bottle shell. The cap has a frangible membrane sealing the cap and the contents of the vessel which is opened by the opening apparatus.

In one aspect of the invention, a protective overcap is secured to the cap to protect the frangible membrane during shipping and handling, which is removed prior to installation of the vessel on the opening apparatus. Additionally, the overcap protects a machine-readable identifier (for example, a radio frequency (RF) identification device or a touch button) removably affixed to the upper portion of the vessel from being accidentally dislodged.

In another aspect of the invention, the lower portion of the bottle shell has a rectangular gripping structure formed from two sets of integral parallel sides and a set of gripping ribs applied to the parallel sides. The gripping ribs assist the user with handling the vessel, particularly when the vessel is being installed in an upside down orientation onto the opening apparatus. The bottom surface of the shell is given a concave shape which prevents the bottle shell from bulging when the bottle and its contents are exposed to high temperatures.

In yet another aspect of the invention, the vessel includes an orientation structure or means cooperating with complementary structure on the opening apparatus for ensuring that the vessel is mounted to the opening apparatus in a predetermined orientation. In this embodiment, the orientation of the vessel relative to the opening apparatus is important to insure that the machine readable identifier is in a position where it can be read by an appropriate reading device. Additionally, in this embodiment, the membrane of the cap is given a frangible (i.e., reduced thickness) section to assist the opening of the vessel. The mounting of the vessel to the opening apparatus in a proper orientation is important to insure that the spike in the opening apparatus makes contact with the membrane in proper alignment with the frangible section.

In still another embodiment of the invention, the cap is provided with a set of saw teeth which cooperates with a set of ratchet or ramp features on the bottle neck to insure that the cap cannot be removed by the user. Thus, the vessel is also tamper resistant.

In still another aspect of the invention, the bottle is designed for use with a machine that features a hot water disinfection cycle, in which hot water (e.g., 80 to 85 degrees C.) is also circulated to the cap membrane to insure disinfection of the interface between the dialysate chemicals and the tank. In this embodiment, the cap is constructed from a material to withstand the high temperature, such as high density polyethylene or polypropylene copolymer.

These and still other features of the invention will become apparent from the following detailed description of presently preferred and alternative embodiments of the invention.

BRIEF DESCRIPTION OF THE DRAWINGS

In the following detailed description of the preferred and alternative embodiments, reference will be made to the accompanying drawings, wherein like reference numerals refer to like elements in the various views, and wherein:

FIGS. 3A–3F are several views of the chemical loading platform of FIG. 2;

FIG. 4 is an elevational view of the vessel and opening apparatus of FIG. 2, showing the spike of the opening apparatus moved to the upper position to pierce the cap's membrane and lift the membrane upwards to promote the release of the contents of the vessel into the tank;

FIGS. 5A and 5B are sectional views of the apparatus for opening of FIG. 4, with FIG. 5A showing the spike in the upper position and FIG. 5B showing the spike in the lower position;

FIG. 9 is a cross-sectional view of the cap of FIG. 7, showing the cap threadably engaging the neck portion of the bottle shell, with the machine-readable identifier shown in phantom;

FIG. 9A is a cross-sectional view of the cap of FIG. 7, showing an alternative embodiment to the overcap;

DETAILED DESCRIPTION OF THE PREFERRED EMBODIMENT

I. Overview and Relationship of Vessel to Machine for Preparing Solutions

Figure 1:
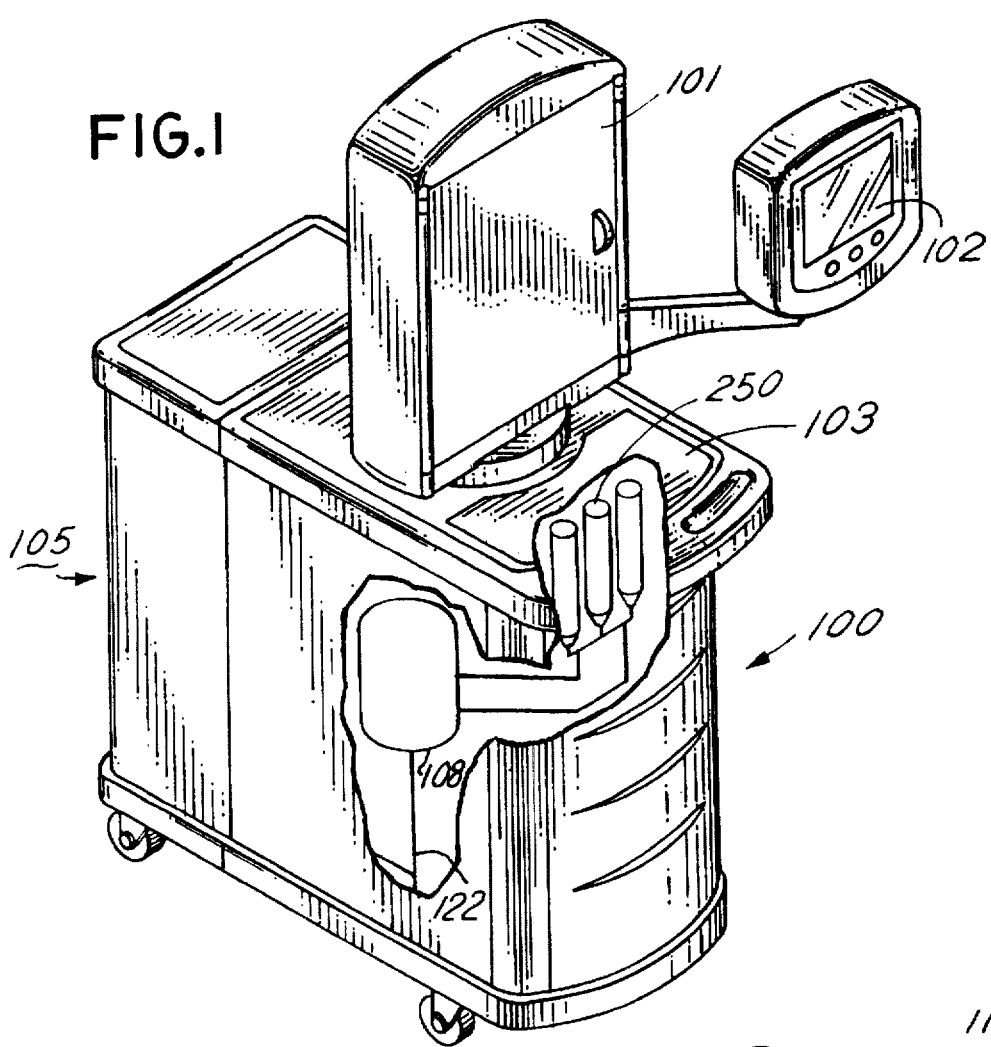
FIG. 1 is a perspective view of a dialysis machine which prepares batch quantities of dialysate from chemicals stored in the vessels of the present invention.

Referring to FIG. 1, the preferred embodiment of a dialysis machine for use in conjunction with the inventive batch chemical vessels is shown in a perspective view. In order to appreciate the various different features of the vessels per se, a discussion of the environment in which they are preferably used is necessary. The preferred manner of using the vessel and dispersing the chemicals stored in the vessels into the solution tank is described in this section in conjunction with FIGS. 1–6. The preferred and alternative embodiments of the subject inventive vessel 250 is illustrated in detail in FIGS. 7–15 and discussed in the next section.

The preferred dialysis machine 100 has an integral water treatment module and dialysate preparation module in a lower cabinet 105. An extracorporeal circuit module is housed within the upper cabinet 101. The machine 100 is preferably a movable unit, with the cabinet 105 mounted on wheels, and is suitable for use in a patient's home environment. The dialysis machine 100 includes a patient interface module 102 including a display and a touch screen connected to one or more central processing units. The interface and control module 102, in conjunction with the central processing units, exercises supervisory control over the operation of the system, displays the current status of the machine, and prompts the user to input commands and information.

The vessels 250 of the subject invention contain batch quantities of chemicals for preparation of physiologic, irrigation, or therapeutic fluids, and are shown in FIG. 1 in an installed condition on the machine 100. When the user wishes to install the vessels 250, the user removes a cover plate 103 from the top surface of the cabinet 105 and installs the vessels 250 in an upside-down orientation on the opening apparatus, as discussed in detail below. The dialysate preparation module within the machine 100 includes a chemical mixing tank 108 sized to prepare a batch quantity of the physiologic fluid, e.g., dialysate.

Figure 2:
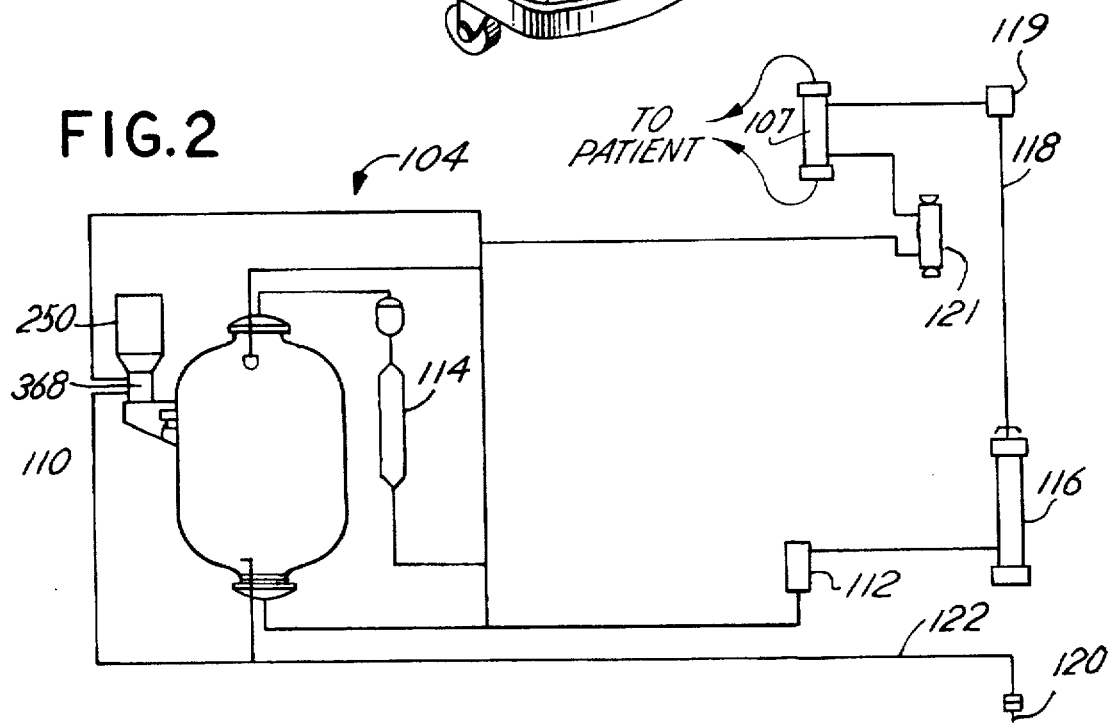
FIG. 2 is a schematic diagram of the dialysate preparation module of the machine of FIG. 1, showing the relationship of the vessels in an installed condition relative to the dialysate preparation tank.

Referring now to FIG. 2, the dialysate preparation module 104 within the machine is shown schematically, with most of the components thereof removed to simplify the present discussion. An overall function of the dialysate preparation module 104 is to automatically mix and prepare the dialysate solutions. The dialysate preparation module 104 has an inlet line 122 connected to a line 120 through which filtered water passes from the water preparation module. The inlet line 122 carries water to the chemical mixing tank 108. A chemical loading platform 110 is attached to the side of the chemical mixing tank 108, and is illustrated in FIGS. 3A–3F. An opening apparatus 368 for opening the vessels 250 and releasing the contents into the chemical loading platform 110 is mounted above the loading platform 110, and is shown in FIGS. 4, and 5A–5C. The chemical vessels 250 are illustrated in detail in FIGS. 7–16.

Referring still to FIG. 2, after the batch quantity of dialysate solution has been prepared in the tank 108, it is pumped via a pump (not shown) past a heater assembly 112. The heater assembly 112 is used for heating dialysate up to body temperature prior to circulation of the dialysate to the dialyzer 107. The heater 112 is also used for heating water to a high level disinfection temperature (e.g., 80 degrees C.) during a hot water disinfection cycle of the machine. Dialysate solution passes through an ultrafilter 116, and then passes via line 118 past a pressure transducer 119 to the dialyzer 107. Blood-borne toxins from the blood in the extracorporeal circuit diffuse through the dialyzer 107 into the dialysate. The dialysate is pumped past a blood leak detector 121 and returned to the top of the tank 108. Some of the dialysate is pumped into an ultrafiltration tank 114 for the purpose of measuring the quantity of fluid removed from the patient.

Figure 3A:
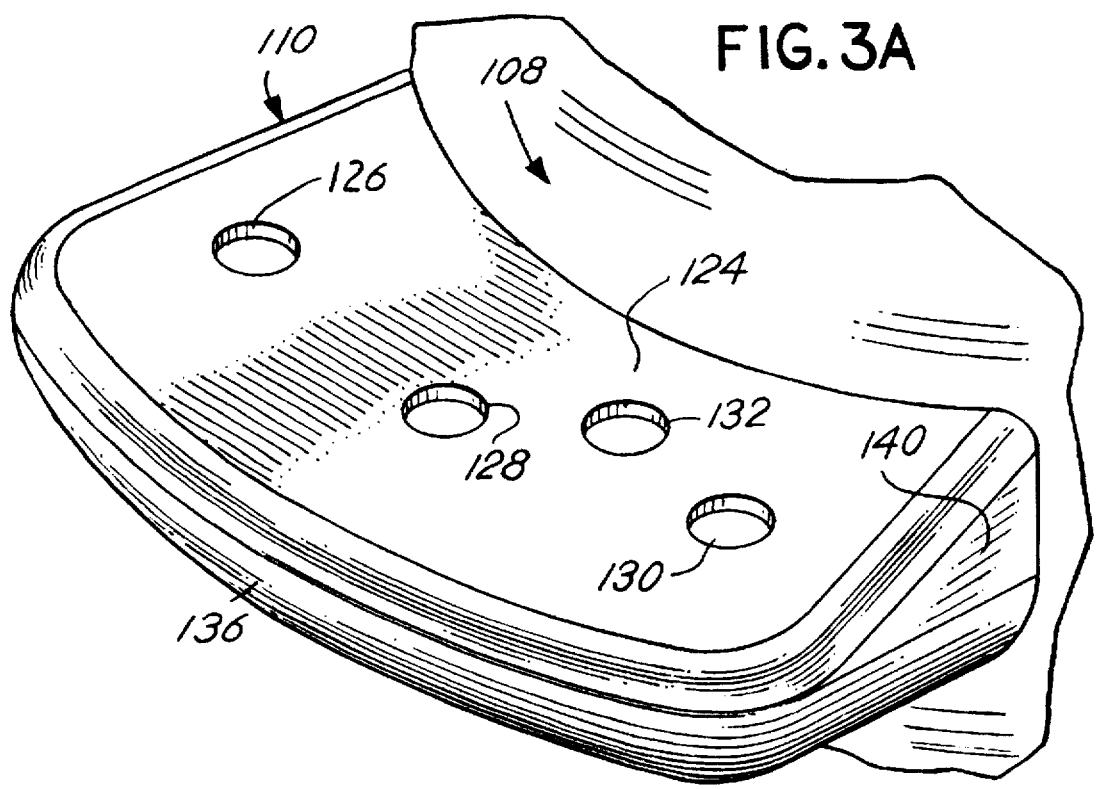
Figure 3B:
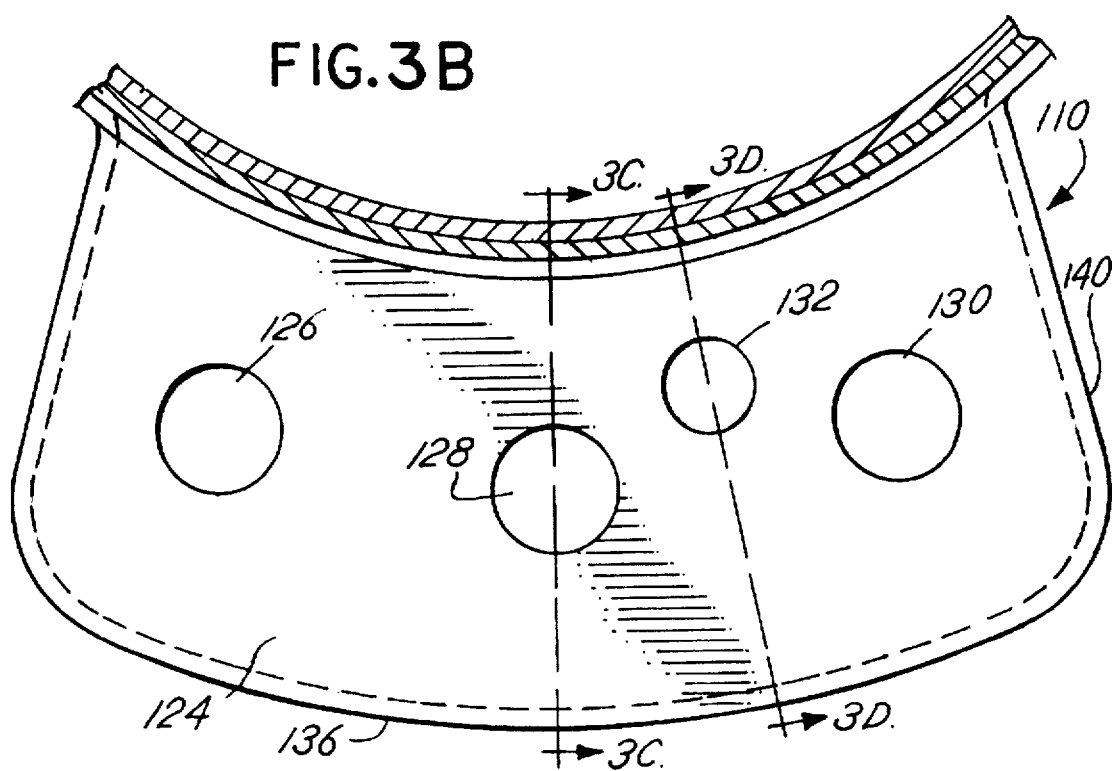
Figure 5C:
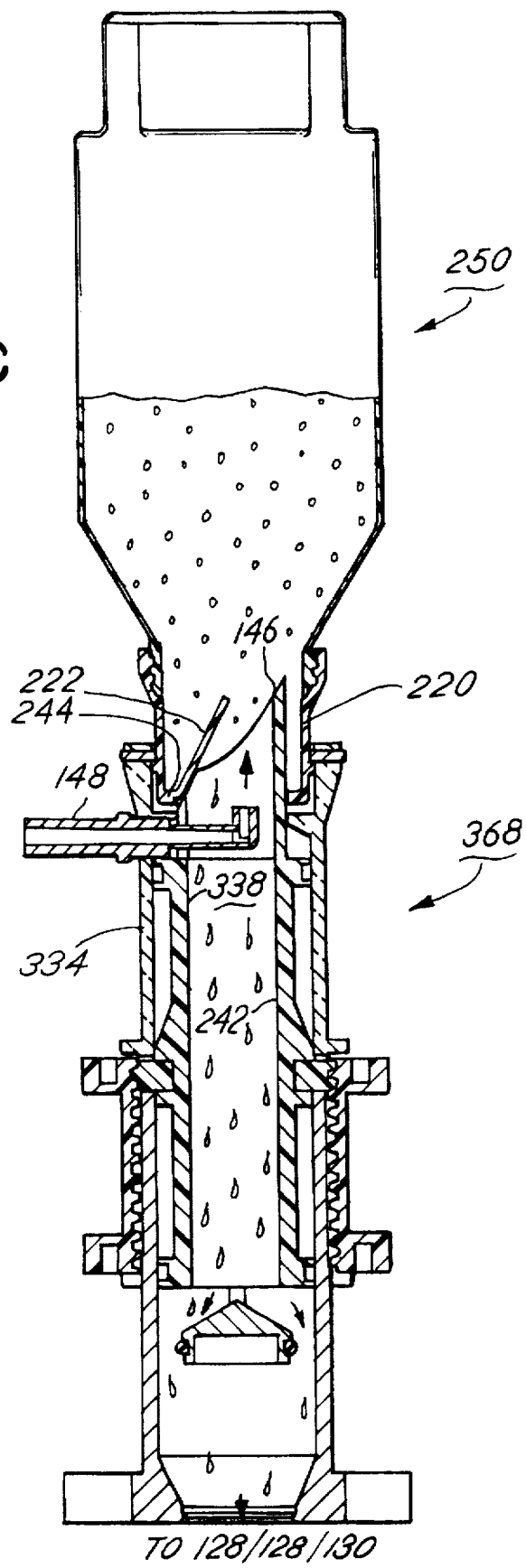
FIG. 5C shows the dispersion of the chemicals in the vessel through the opening apparatus into the loading platform of FIGS. 2 and 3A–3F.
Figure 6A:
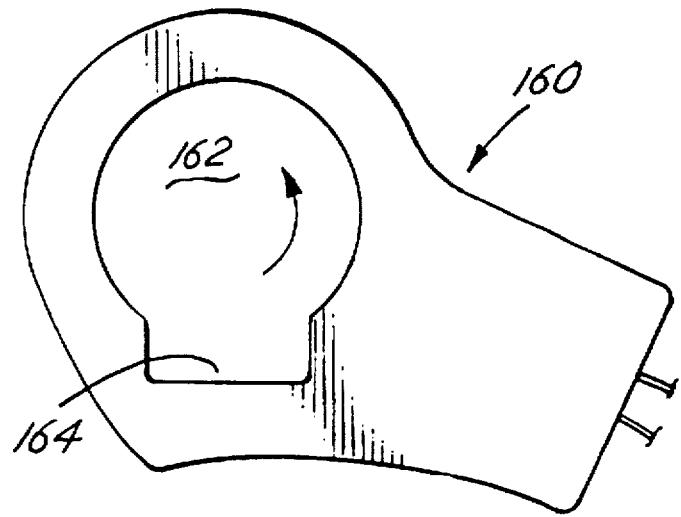
FIG. 6A, 6B and 6C are several views of the mounting and orientation member of FIG. 5A and 5B, showing the solenoid mechanism controls removal of the machine readable identifier.
Figure 6B:
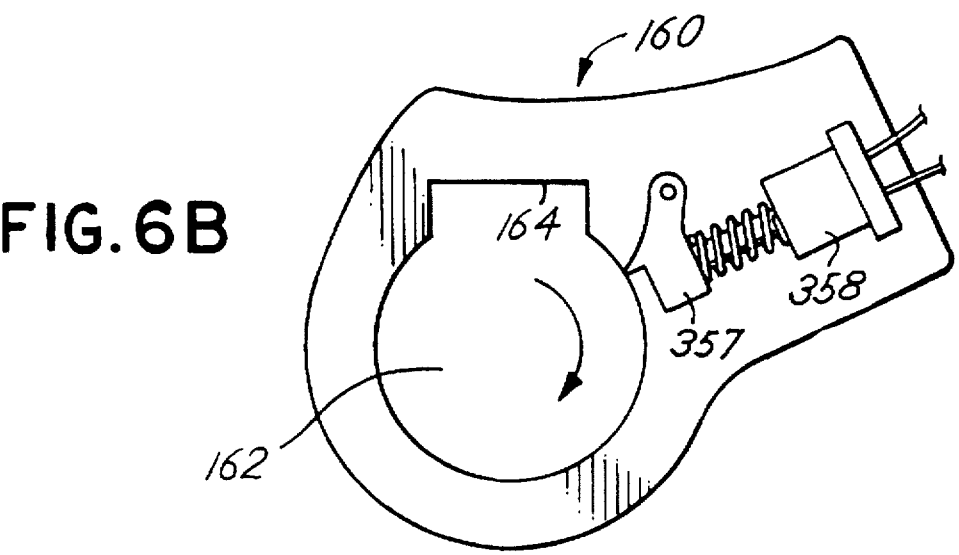
Figure 6C:
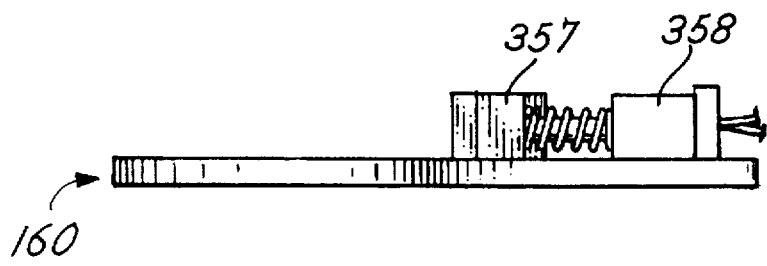

Referring to FIGS. 3A–3F, the chemical loading platform 110 of FIG. 2 is shown in several views. FIG. 3A is a perspective view of the platform 110 shown positioned against the side of the chemical mixing tank 108. FIG. 3B is a top plan view of the platform 110. FIG. 3E is an elevational view of the platform 110. The platform 110 is an integrally molded housing mounted to the side of the chemical mixing tank 108 having a top 124 with four apertures. Apertures 126, 128 and 130 provide passageways for chemicals to be released from the vessels 250 (FIG. 2), through the apparatus 368 for opening the vessels 250, and into the tank 108. Opening 132 is for a sprayer suspended within the platform 110. The opening apparatus 368 (FIG. 2), one per vessel, is installed above the top 124 of the platform 110. The lower shelf 134 of the platform 110 is inclined at an angle of between 10 and 30 degrees (preferably 17 degrees) relative to the horizontal to promote dispersion of chemicals delivered onto the shelf 134 into the chemical mixing tank 108. The platform further has a rim 136 and sidewalls 140.

Referring in particular to FIG. 3C and 3D, an aluminum plate 144 is mounted to the top 124 of the platform 110 to provide a mounting base for the apparatus 368 for opening the vessels (FIGS. 2, 4, 5A–5C).

Referring to FIG. 3D, a sprayer 142 connected to the water lines in the machine is provided for spraying fluids (e.g. purified water) in the direction of the lower shelf 134 to assist in washing chemicals off the shelf 134 and into the chemical mixing tank 108. The sprayer 142 promotes effective dissolution of the chemicals within the chemical mixing tank 108 and avoids the buildup of chemicals on the shelf 134. The sprayer is positioned below the aperture 132 in the top of the platform 110.

Three apparatus 368 for opening the vessels 250 are mounted to the plate 144 directly above the apertures 126, 128 130, one of which is shown in detail in FIGS. 4 and 5A–5C. Typically, only two vessels are needed to prepare a dialysate solution, with one vessel containing powdered dialysate chemicals and the other containing dialysate chemicals in liquid form. When the chemical mixing tank 108 is filled with purified water to the proper level, an extendable spike 242 in the opening apparatus (FIGS. 5A–5C) moves upwards to pierce a membrane 222 sealing the vessels 250, causing the chemicals to fall out of the bottles 250 into the loading platform 110. The sprayer 142 washes the chemicals deposited on the lower shelf 134 of the loading platform 110 into the tank 108.

A third vessel 250 and opening apparatus 368 are also preferably provided above the platform 110. The chemicals in the third vessel will typically either be salt or buffer solution which can be added to the dialysate solution on demand to adjust or change the chemistry of the dialysate solution, or else disinfecting agents, medications, vitamins or other nutritional supplements.

Referring to FIGS. 4 and 5A–5C, the opening apparatus 368 has a cylindrical housing 334 mounted to a base member 336 affixed to the aluminum plate 144. The housing 334 has an open interior region 338. A threaded drive collar 340 is mounted to the housing 334. A spike 242 is reciprocable within the interior region 338 between upper and lower positions. The spike 242 pierces the seal or membrane 222 on the vessel 250 when the spike 242 is moved to the upper position (FIG. 4, 5C). The spike 242 has an integral cylindrical body concentric with the housing 334 with an open cylindrical interior for permitting passage of dialysate chemicals therethrough after the spike 242 has pierced the membrane 222.

A pair of thread blocks 344 are mounted to the side walls of the spike 242 which engage threads 346 on the interior of the drive collar 340. As shown in FIG. 4, a drive belt 348 (one or two) or other suitable means (such as a cog or pinion) engages the threaded drive collar 340. As the belt 348 rotates the collar 340, the thread blocks 344 are rotated, causing the spike 242 to move between the upper and lower positions depending on the direction of movement of the drive belt 348.

Referring in particular to FIGS. 4, 5A, 5B and 5C, a nozzle 148 is disposed within the cylindrical housing 334 in communication via a water line. The cylindrical body 242 of the spike has a vertical slit to accommodate the nozzle 148. The tip 152 of the nozzle 148 is oriented upward in the direction of the vessel 250. The flow of water through the nozzle 148 on demand ejects water towards the interior of the vessel 250 after the bottle has been opened by the spike 242, thereby rinsing the interior of the vessel 250 and promoting the release by gravity of the entire contents of vessel 250 through the aperture 126 (or 128, 130) and into the tank 108. To control the dispensing of dry dialysate chemicals from the bottle, and prevent clogging of chemicals at the base of the bottle, we prefer to pulse water through the nozzle 148 over a period of time. For example, water is pulsed through the nozzle for one second (with a pressure greater than 10 psi), then there is a brief pause while some of the chemicals fall through the interior of the spike 242, then and another pulse, a pause, and the process continues until all the chemicals have fallen out of the bottle. This pulsing may occur for perhaps 50 times over a ten minute period. This pulsing action prevents all of the chemicals from being dumped at once onto the shelf of the loading platform. When the bottle is substantially empty, the nozzle rinses out the bottle with a continuous stream of water of 5 to 10 seconds duration.

The nozzle 148 also ejects heated water (or water treated with disinfecting chemicals) onto the outside surface of the seal 222 of the vessel 250 during the disinfection cycle of the machine, thereby disinfecting the interface between the chemicals in the vessel 250 with the dialysate preparation tank 202.

Referring now in particular to FIGS. 4 and 6A–C, together with FIG. 9, a bottle mounting and orientation member 160 is placed above the housing 334 of the opening apparatus 368 to insure that the bottle 250 is mounted in alignment with the spike 242 and in condition for a reading device to read a machine readable identifier affixed to the vessel. The mounting and orientation member 160 is shown in a top plan view in FIG. 6A (i.e., as it would be seen when looking down from above in the direction of the top of the spike), in a bottom plan view in FIG. 6B, and in a side elevational view in FIG. 6C. The mounting member 160 has a central opening 162 through which the cap 220 of the vessel 250 is inserted. (The overcap 224 in FIG. 9 will be removed prior to this step). A notch 164 accommodates a machine readable identifier 366 (FIG. 9) that is affixed to the cap 220 and the retaining structure for the machine readable identifier. The machine readable identifier (such as the "Dallas memory button" available from Dallas Semiconductor Corp., Dallas Tex.), contains coded information as to the contents of the vessel 250. The outward projection of the machine readable identifier and its associated retaining structure cooperates with the notch 164 of the mounting and orientation member 160 to insure that the bottle can be mounted to the opening apparatus 368 in only one position.

The mounting member 160 has a pawl 357 that is retractable by operation of an electric solenoid 358 for controlling the removal of the machine readable identifier 366 when the vessel 250 is removed from the mounting member 160. During installation of the vessel 250, the head of the vessel 250 (turned "upside down") is placed within the opening 162 and rotated in the direction of the arrow of FIGS. 6A and 6B into threaded engagement with the housing 334 (FIG. 4). The machine readable identifier 366 slides past the pawl 357 into contact with a suitable machine readable identifier reader. When the vessel 250 is removed from the opening apparatus 368, the bottle must be rotated in the opposite direction. Pawl 357 is activated by solenoid 358 to an extended position. When the bottle is rotated such that the machine readable identifier is rotated past the pawl 357, the pawl 357 pushes the machine readable identifier 366 off of the bottle cap portion 220, causing it to fall. A suitable catchment structure is provided about the apparatus 368 and aluminum shelf 144 to catch and collect the fallen machine readable identifiers. The user of the machine collects the buttons and sends them back to a collection center for reprogramming and reuse. Alternatively, the buttons 366 could be collected by a service technician during a service visit.

II. Vessel 250 Detailed Description

Figure 7:
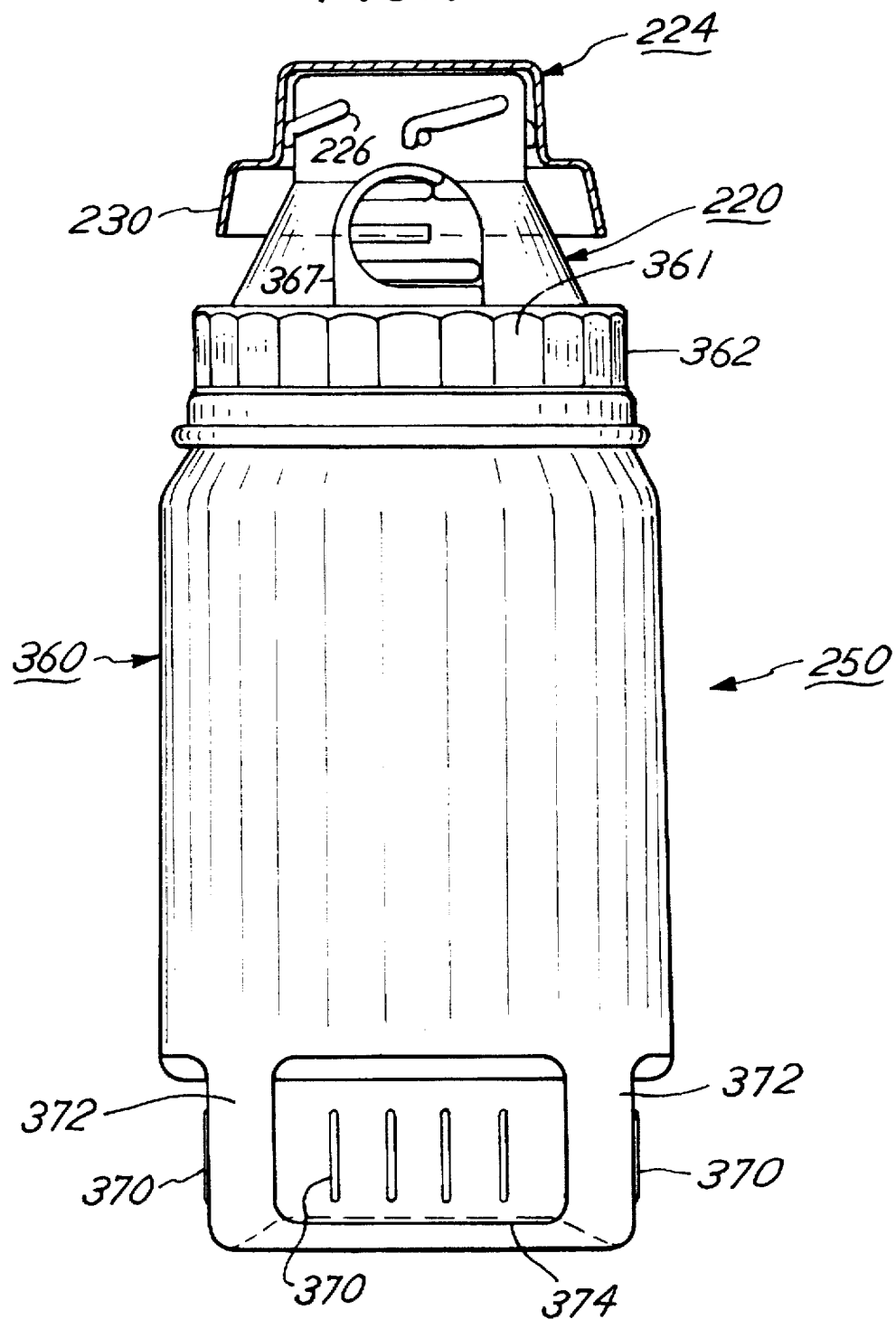
FIG. 7 is a detailed elevational view of the vessel of FIGS. 1, 2, 4 and 5 according to a preferred form of the invention.

Having described the environment in which the vessel 250 is preferably used, the vessel per se 250 will be discussed in detail in conjunction with FIGS. 7–15. Referring now to FIG. 7, the preferred embodiment of the inventive vessel 250 is shown in an elevational view in a fully assembled condition. Preferably, the vessel 250 contains a batch quantity of chemicals for preparation of physiologic, therapeutic, or irrigation fluids, such as a unit batch of liquid or dry chemicals for dialysate. The vessel 250 comprises a generally cylindrical bottle shell 360 and a cap 220 that screws onto the bottle shell 360. The cap 220 has a manually manipulable rim portion 362 having threads on its interior surface that engage complementary features on the neck portion the bottle shell 360. The vessel 250 further has a protective overcap 224 covering the top of the cap 220. The overcap 224 is removably mounted to the cap 220 by engagement of the overcap to the threads 226 on the cap 220. The overcap 224 serves to protect the membrane at the top of the cap 220 during shipping and handling of the vessel 250.

The cap 220 has a touch button retaining structure 367 that retains the machine-readable identifier 366 (FIG. 9) in a manner such that the machine readable identifier is removably affixed to the cap 220. The overcap 224 also has a lower skirt portion 230 that protects the machine readable identifier from being accidentally removed from the retaining structure 367 during shipping and handling.

The rim 362 of the cap 220 has scalloped-shaped features 361 around the periphery thereof. The scalloped shaped features 361 are needed for the automatic capping machine to grip the cap 220 and screw the cap 220 onto the bottle shell 360 during the assembly of the bottle.

The lower portion of the bottle shell 360 has a generally rectangular structure comprising opposed pairs of integral parallel sides 373 having corners 372. A set of vertically disposed gripping ribs 370 are applied to the lower portion of the bottle shell 360 to assist the user when handling the vessel 250, and especially when installing the vessels 250 in the machine 100. The bottom of the shell 360 has a concave surface 374 to prevent the bottom of the bottle shell 250 from bulging outwardly when the vessel 250 is exposed to high temperatures, such as during the hot water disinfection process or during shipping.

Figure 8:
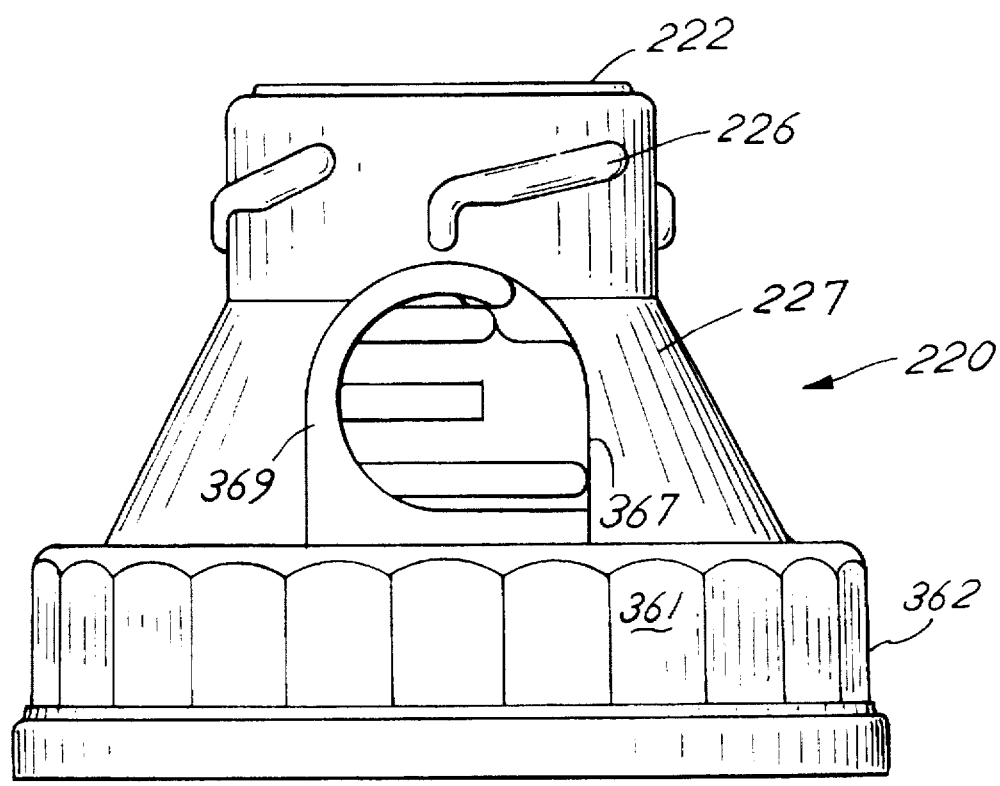
FIG. 8 is a detailed elevational view of the cap of FIG. 7, showing the retaining structure for a machine-readable identifier.

FIG. 8 is a detailed elevational view of the cap 220 with the protective overcap 224 removed. The cap 220 covers the bottle shell 360 and has an integral manually manipulable rim 362 that threads the cap 220 onto the bottle shell 360. A frangible membrane 222 at the top of the cap seals the cap 220. The upper exterior portion of the cap 220 has a set of threads 226 for mounting the vessel 250 to the apparatus 368 (FIG. 4) for opening the vessel 250. The machine readable identifier retaining structure 367 has a rim 369 that receives the edge of the machine readable identifier when the identifier is slid into the structure 367. When the cap 220 is inserted through the plate 160 (FIG. 6A), the retaining structure 367 is inserted through the notch 164 (FIG. 6A), insuring that the vessel is mounted in a pre-determined position or orientation. This insures that the machine readable identifier is in position for reading and that the spike engages the frangible membrane in the desired position.

FIG. 9 is a cross-sectional view of the cap 220 and overcap 224. The overcap 224 protects the frangible membrane 222 from puncture during shipping and handling. A set of serrated ribs 228 on the interior portion of the overcap 224 serve to engage the overcap 224 to the cap threads 226. This insures that the overcap 224 remains in a secure position attached to the cap 220 until the time comes to install the vessel 250 in the machine. The overcap 224 is removed prior to installation of the bottle on the opening apparatus. The lower portion of the overcap 224 has a skirt portion 230 that protects the machine-readable identifier 366 from being accidentally dislodged during the handling of the vessel 250, while allowing the machine readable identifier to be programmed or read with the overcap in place.

A set of slanted saw teeth 364 are circumferentially disposed on the extreme lower portion of the rim 362, facing inwardly towards the bottle shell 360. The saw teeth 364 insure that the cap 220 cannot be removed from the bottle shell 360 after the chemicals have been loaded into the bottle shell and the cap 220 installed during manufacture. Referring to FIGS. 9, 10, 12 and 13, the bottle shell 360 has a set of ratchet or ramp projections 365 positioned on opposite sides of the upper portion of the neck 361, immediately below the threads 363. When the cap 220 is threaded onto the threads 363 of the bottle shell, the slanted surfaces 380 of the saw teeth 364 slip over the slanted surfaces of the ramps 365. When the cap 220 is completely threaded onto the shell 360, the saw teeth 364 (FIG. 9) are at the same elevation as the ramp projections 365 (FIG. 12) on the exterior of the shell 368. If the user were to attempt to remove the cap 220 by twisting the cap 220 in the opposite direction, the surfaces 382 of the saw teeth engage the end portions 371 of the ramps, preventing the cap 220 from being removed.

Figure 9B:
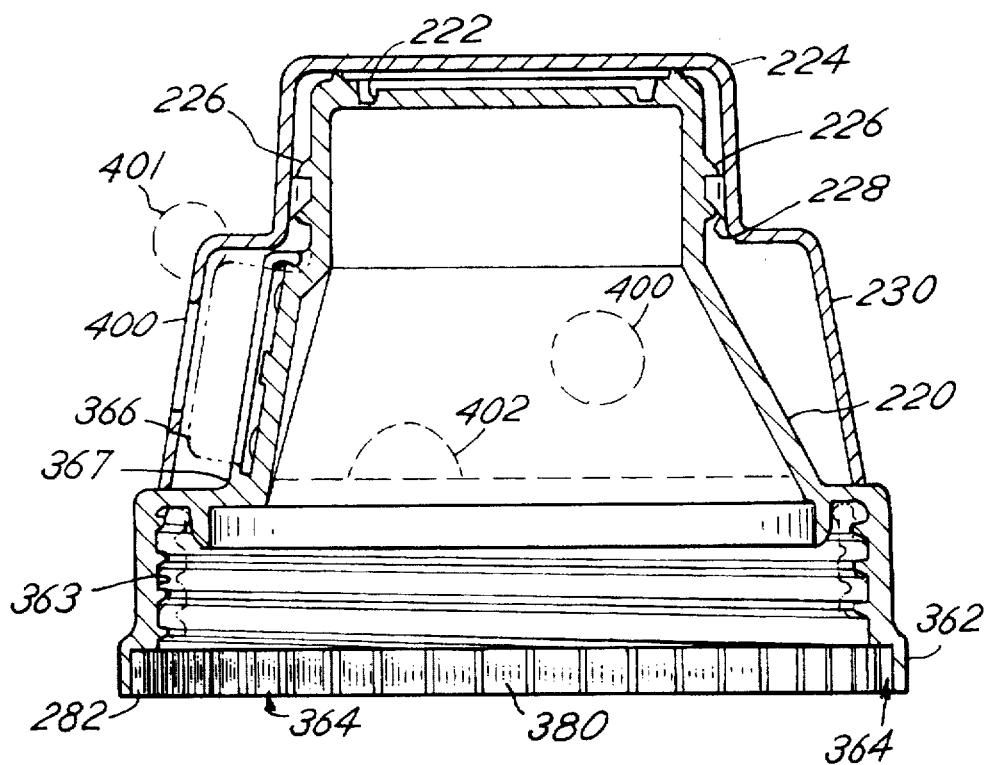
FIG. 9B is a cross-sectional view of the cap of FIG. 7, showing another alternative embodiment to the overcap.

FIG. 9A shows an alternative embodiment of the overcap 224. In this embodiment, the overcap 224 is short and serves to basically protect the frangible membrane 222 during shipping and handling. The machine readable identifier 366 is securely affixed to the cap 220 to prevent accidental removal thereof. FIG. 9B shows another possible alternative embodiment of the overcap 224. In the embodiment of FIG. 9B, the overcap 224 has a long skirt portion 230 that extends over the upper portion of the cap 220 as shown. This overcap protects both the frangible membrane 222 and the machine readable identifier 366. This design provides protection against physical removal of the machine readable identifier before use by the patient. One or more holes 400, perhaps four in all, are provided in the side walls of the overcap 230, and can be placed at roughly the same elevation of the machine readable identifier 366 or slightly higher in the corner region 401 of the overcap 224. When the overcap 230 is installed, one of the holes 400 will be opposite the identifier 366 to allow for programming in situ of the machine readable identifiers during manufacturing, with the overcap 224 installed. Alternatively, a set of cutouts 402 can be provided along the bottom of the skirt which allow communication between the machine readable identifier 366 and a reading/programming device. Note that if the machine readable identifier 366 is a RF type of device, the programming device is a proximity device and need not come into physical contact with identifier. On the other hand, if a touch button is used for the identifier 366, then the programming device must come into contact with the identifier 366.

A seal feature is provided between the bottle shell 360 and the cap 220 when the cap 220 is threaded onto the bottle shell 360. This feature is shown in FIG. 9, and shown greatly enlarged in FIG. 16. Referring to these figures, the base of the bottle cap 220 includes a circumferential, downwardly depending plug element 409 with a curved surface 411. As the cap 220 is threaded onto the threads 363 of the bottle shell 360, the curved surface 411 engages interior surface 417 of the bottle shell 360 (see FIG. 16), causing the upper region of the bottle shell 423 to be bent or deformed slightly (represented by the dashed lines 417') and pressed into a tight fit between the plug element 409 and the thread-engaging shelves 405 and 407 of the cap 220. This seal, known in the art as a "plug seal", generally represented by reference numeral 419, exists even if the cap 220 is not completely torqued down on the bottle shell 360. The plug seal 419 is considered the primary seal between the cap and the bottle shell, and prevents any leakage of the contents of the vessel. A secondary seal represented by numeral 421 is created when the cap 220 is fully torqued down on the bottle shell 360. This seal 421 is created between the top 413 of the bottle shell 360 and a circumferential rib projection 415 provided on the cap 220 body. This secondary seal 421 prevents dust, microbial agents, or other contaminants from coming into the space between the portion 423 of the shell and the plug 409, and also acts as a backup seal in case the primary seal 419 fails.

Figure 10:
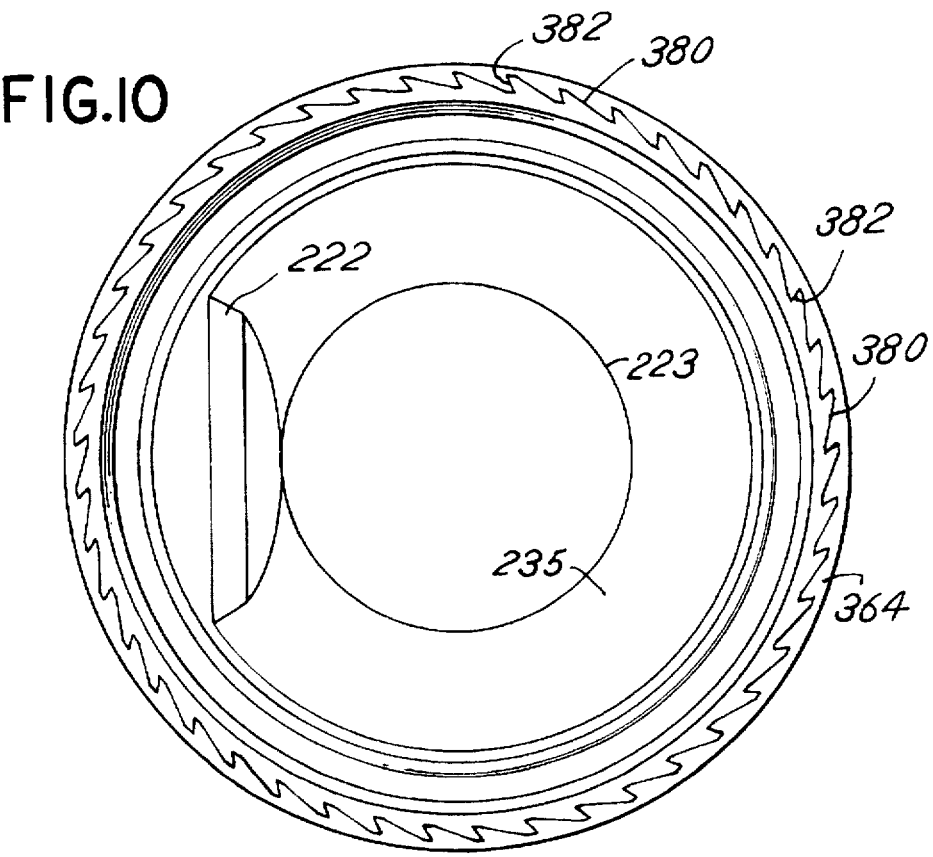
FIG. 10 is a plan view of the cap of FIG. 8 with portions of the peripheral region of the cap removed in order to show the saw teeth, with the frangible membrane in an upward orientation as it would be when the spike has pierced the membrane.

FIG. 10 is a top plan view of the cap 220, with most of the peripheral cap structure removed in order to show the saw teeth 364. The central section of frangible membrane 222 is shown in an upward position, as it would be after the spike 242 in the opening apparatus has opened the vessel.

Figure 11A:
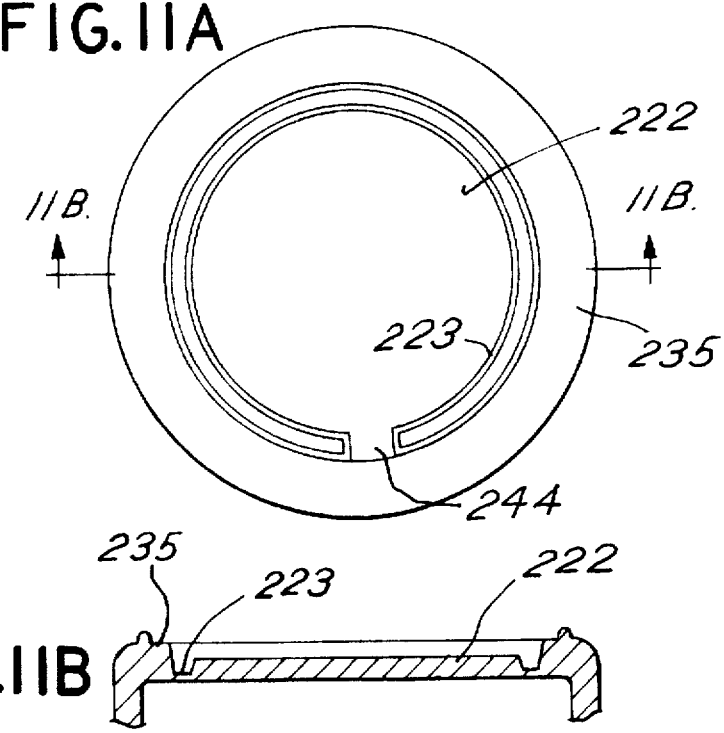
FIGS. 11A–11L are several views of six alternative configurations for the cap's frangible membrane.
Figure 11B:
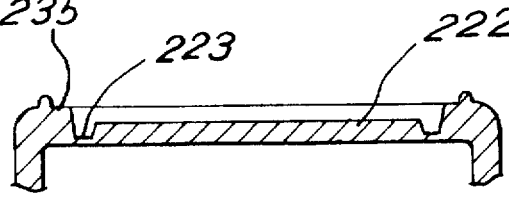

The membrane 222 of the cap is shown isolated from the cap 220 in FIG. 11A. The membrane construction of FIG. 11A is shown in a sectional view in FIG. 11B. Several alternative constructions to the frangible membrane are envisioned. The frangible membrane must be strong enough that the spike will lift the membrane up when it pierces the membrane, but not too strong. The alternatives discussed here are suitable for a membrane 222 made from high density polyethylene or polypropylene copolymer. The basic structure of the frangible membrane 222 is shown in FIGS. 11A-11B. The membrane 222 has a thickness of between 25-30 mils, except for the frangible section 223 which has a thickness of up to 15 mils. The section 223 is thinner than the rest of the membrane 222 in order to assist the spike in cleanly tearing the membrane as the spike 242 (FIG. 5C) is moved upwards. The peripheral portion of the membrane 235 can be thicker than the central portion 222 if desired.

The membrane construction of FIG. 11A includes a hinge portion 244 with a thickness of between 25 and 30 mils. The hinge 244 is provided to keep the central portion of the membrane 222 attached to the peripheral portion 235 when the spike 242 opens the vessel, thereby insuring that the membrane 222 does not fall into the dialysate tank or cause an obstruction as the chemicals are being removed from the vessel. When the vessel 250 is properly mounted to the opening apparatus (FIG. 4, 5A–5C), the spike 242 is positioned below the membrane 222 such that the uppermost portion of the spike tip 146 first contacts the portion of the membrane opposite the hinge 244. As the spike moves upwards, the upper rim of the spike 242 tears through the frangible section 223 of the membrane, but the spike's travel is limited so as to not cut through the hinge 244.

Figure 11C:
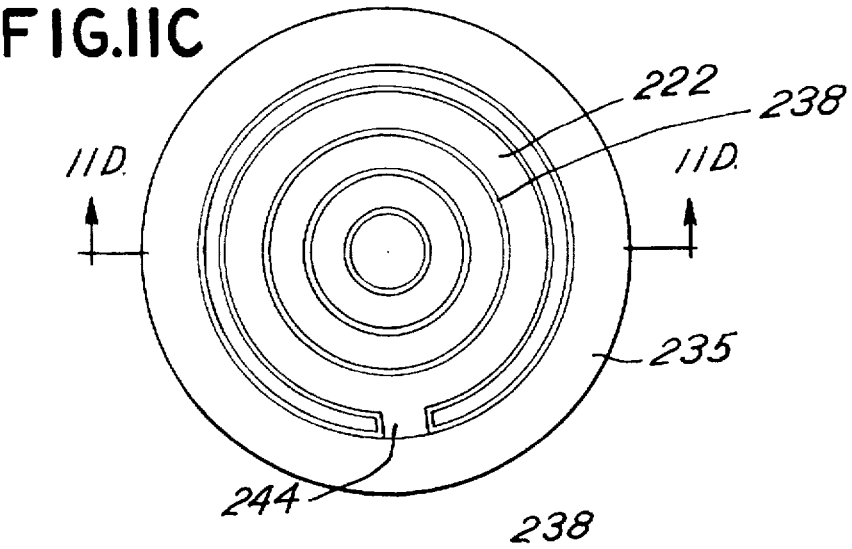
Figure 11D:
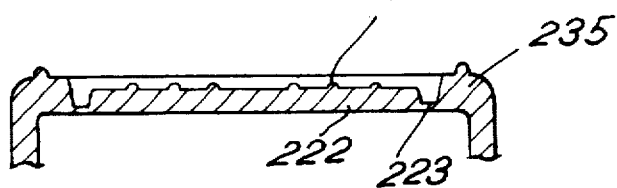

FIG. 11C shows an alternative arrangement in which a set of concentric reinforcing ribs 238 are incorporated into the central portion of the membrane 222. The reinforcing ribs 238 serve to stiffen the membrane 222 and help insure that the membrane 222 remains intact as the spike tears through the frangible section 223. The alternative embodiment of FIG. 11C is shown in cross-section in FIG. 11D.

Figure 11E:
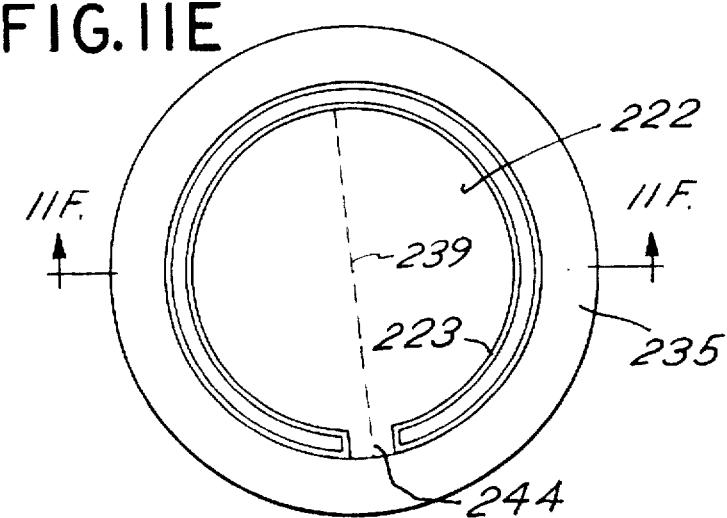
Figure 11F:
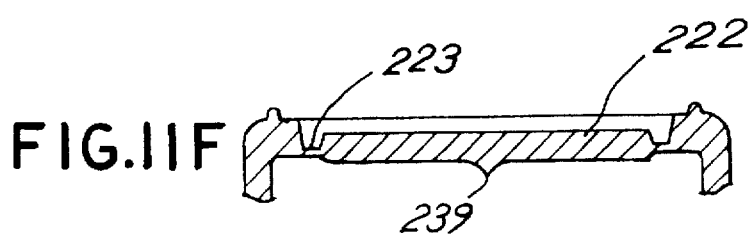

Another alternative is shown in FIG. 11E, in which a reinforcing material with a central ridge 239 is applied to or molded into the interior side of the membrane 222. The structure of FIG. 11E is shown in a sectional view in FIG. 11F.

Figure 11G:
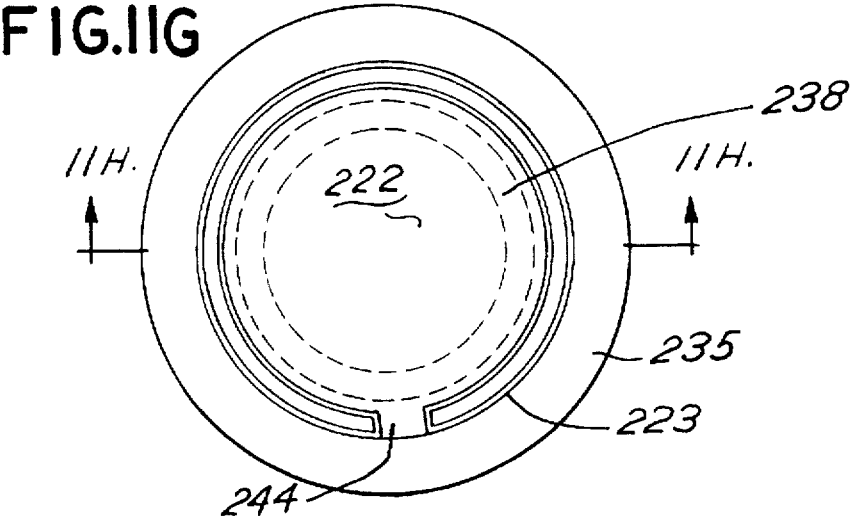
Figure 11H:
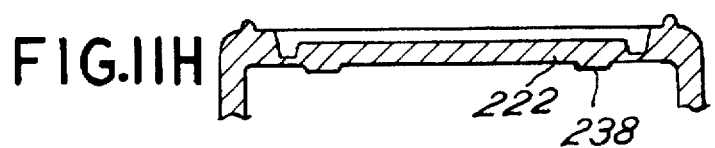

Another alternative is shown in FIG. 11G. A circular reinforcing ring structure 238 is molded into the interior side of the membrane 222. This construction is shown in a sectional view in FIG. 11H.

Figure 11I:
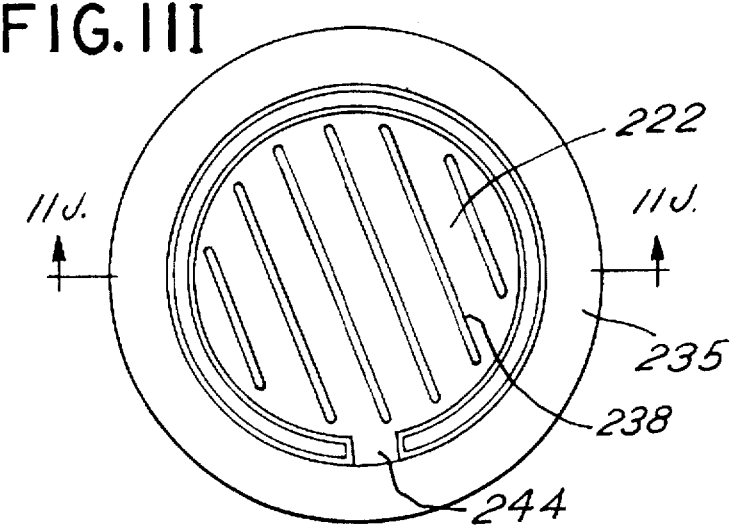
Figure 11J:
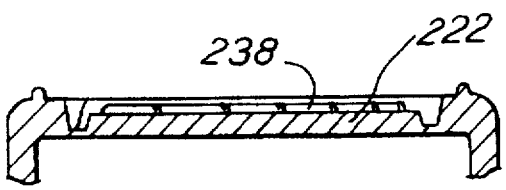

Another alternative is shown in FIG. 11I. A set of parallel reinforcing ribs 238 are applied to the exterior portion of the membrane 222. This construction is shown in a sectional view in FIG. 11J.

Figure 11K:
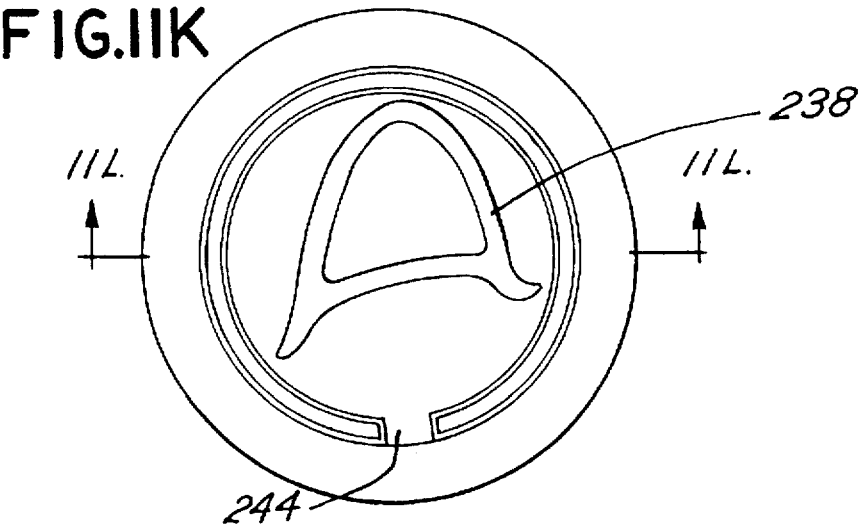
Figure 11L:
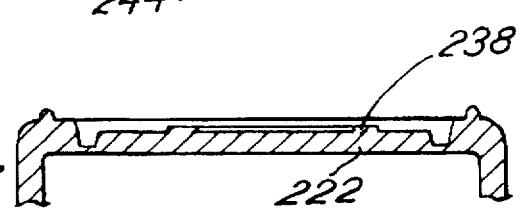

Yet another alternative embodiment is shown FIG. 11K. Here, the reinforcing structure 238 takes the form of a letter (such as trademark, logo or other identifying symbol) which extends outwardly from the exterior surface of the membrane 222. This construction is shown in a sectional view in FIG. 11L.

Figure 12:
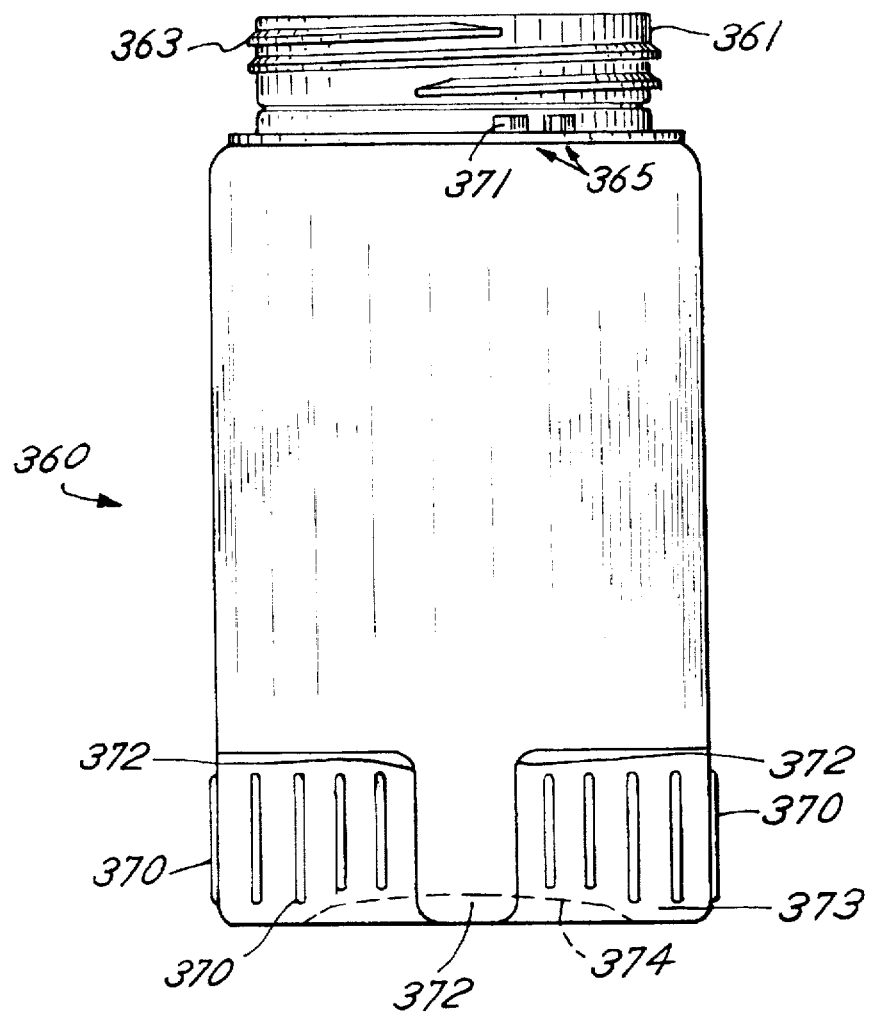
FIG. 12 is an elevational view of the bottle shell, rotated 45 degrees from the orientation illustrated in FIG. 7, illustrating the ratchet or ramp features of the neck of the bottle shell and the gripping ribs on lower exterior portion of the bottle shell.

Referring now to FIG. 12, the bottle shell 360 is shown isolated and rotated 45 degrees from the orientation of FIG. 7. The lower exterior portion of the bottle shell 360 has the gripping ribs 370 applied to the bottle shell 360. In an alternative embodiment, the ribs 370 are applied parallel to a plane defined by the bottom of the bottle shell 360 (i.e. horizontally), or else in an inclined orientation.

Figure 13:
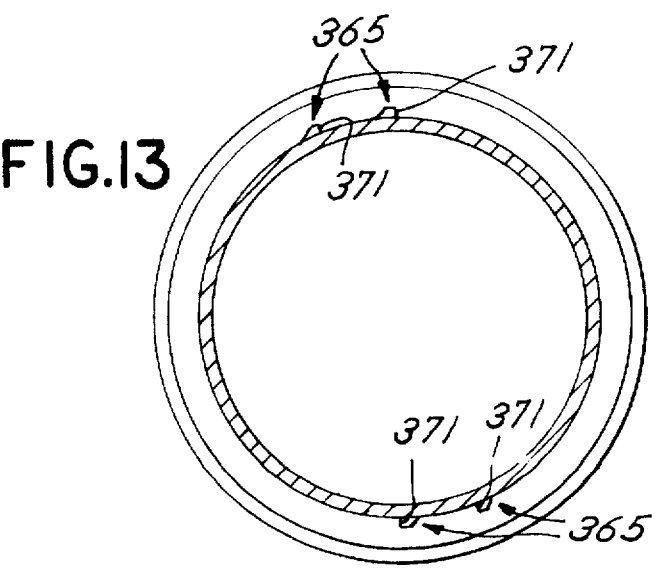
FIG. 13 is a top plan view of the bottle shell of FIG. 12.

FIG. 13 is a top plan view of the shell 360, showing the sets of ratchet or ramp projections 365 which cooperate with the saw teeth on the cap 220 to prevent removal of the cap. While only two pairs of ratchet projections 365 are shown in this embodiment, it will be understood that additional pairs of projections can be used, and that the ratchet projections could consist of one pair, two pairs, four pairs, or as many as can be conveniently fit on the bottle shell.

Figure 14:
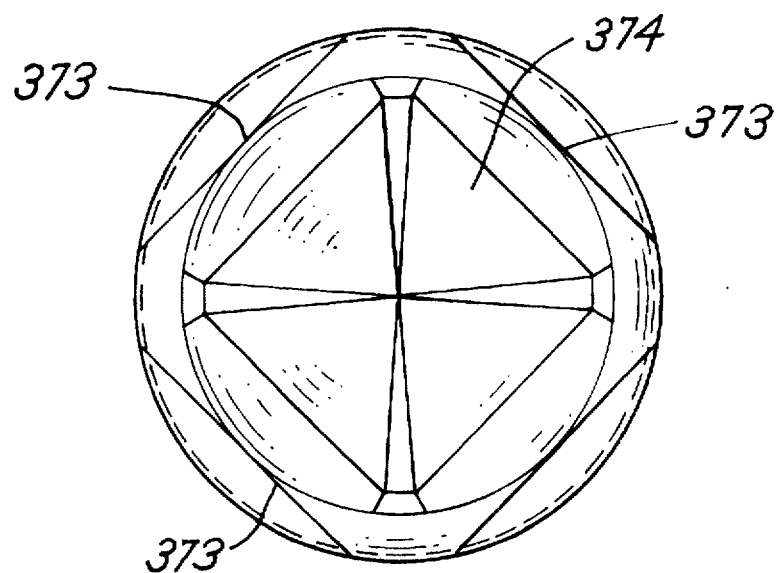
FIG. 14 is a plan view of the bottom surface of the bottle shell.
Figure 16:
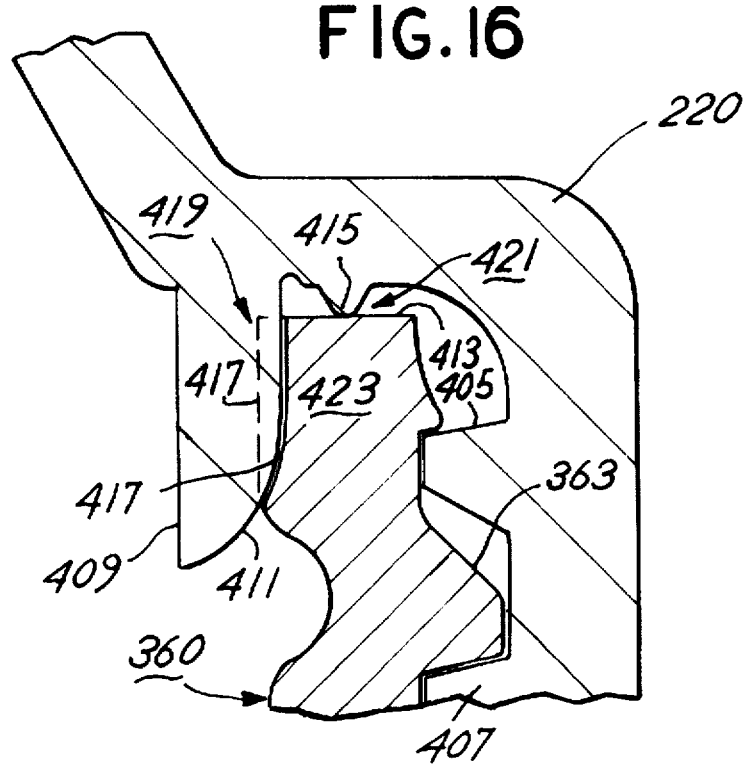
FIG. 16 is a detailed view of the seal area between the cap and bottle of FIG. 9.
Figure 15A:
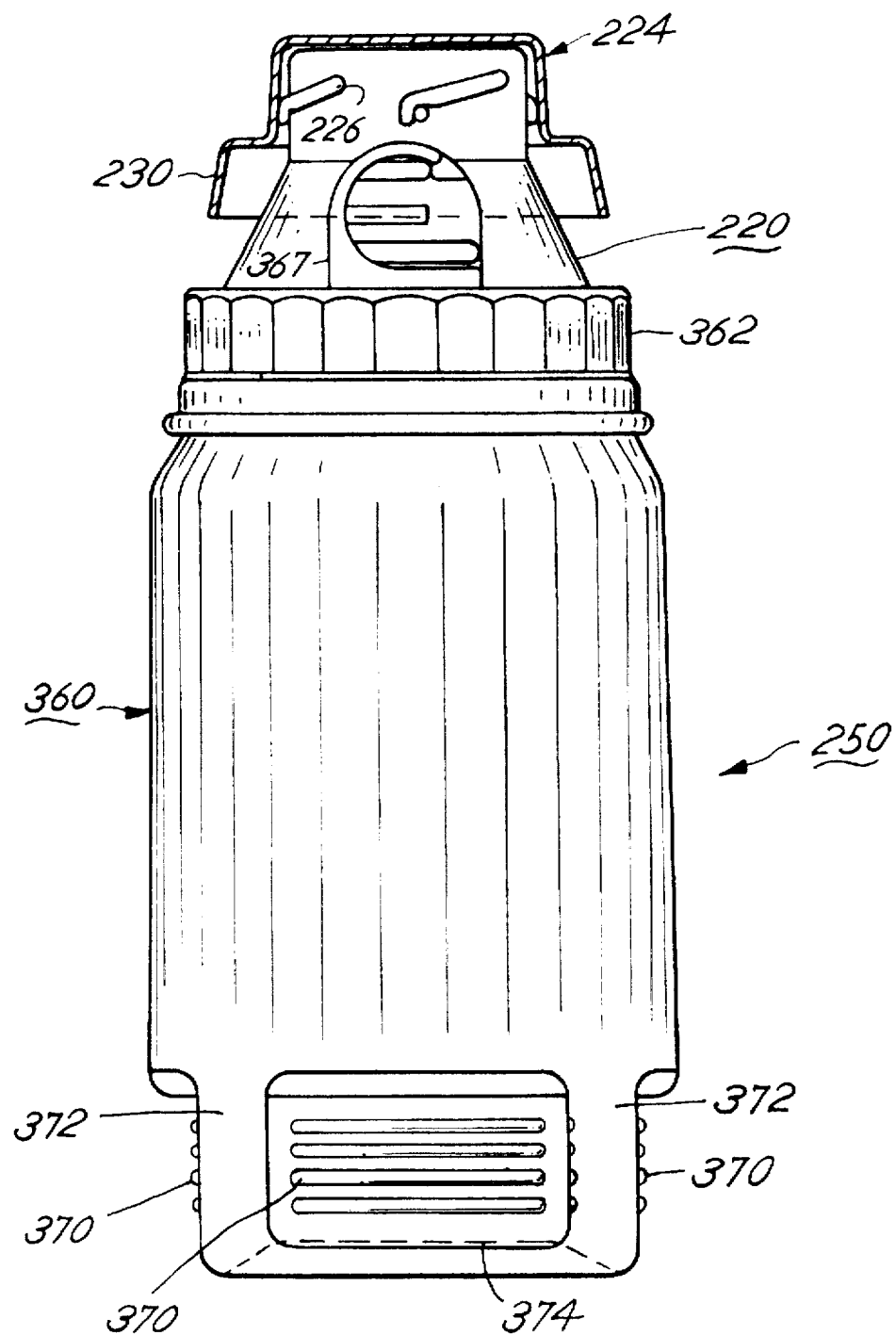
FIGS. 15A–15D are illustrations of various alternative gripping arrangements for the lower portion of the bottle shell from the embodiment shown in FIGS. 7 and 12.
Figure 15B:
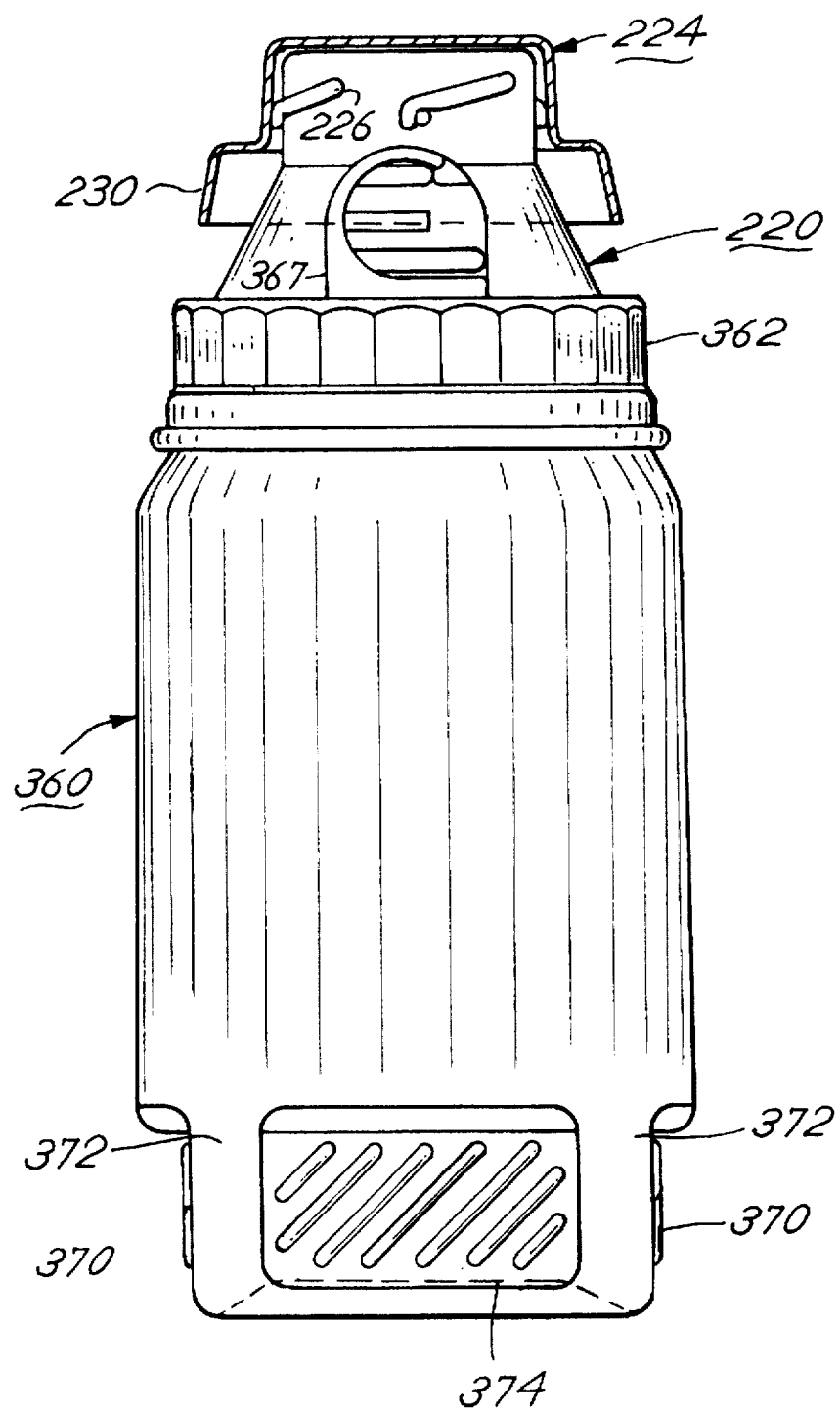
Figure 15C:
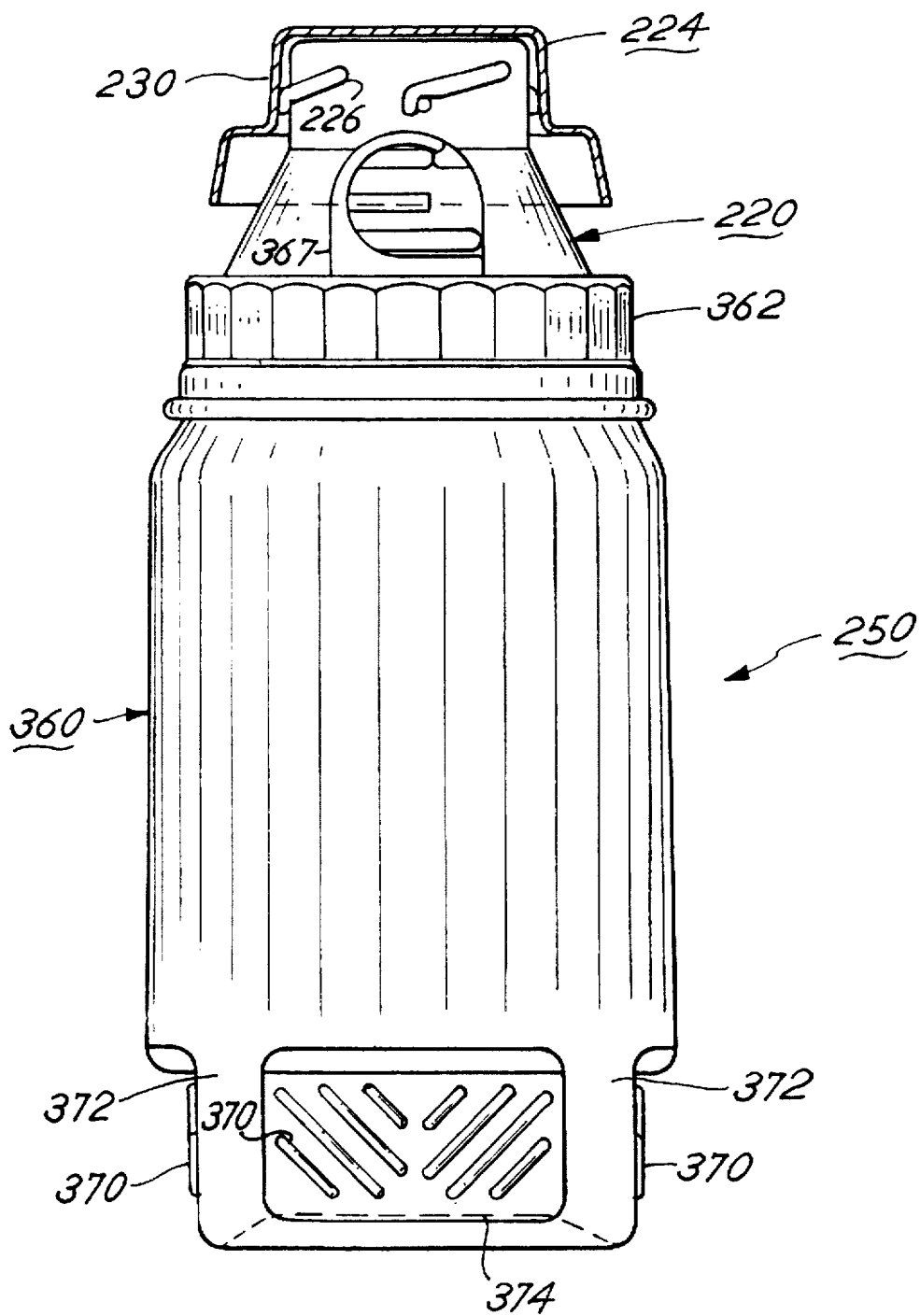
Figure 15D:
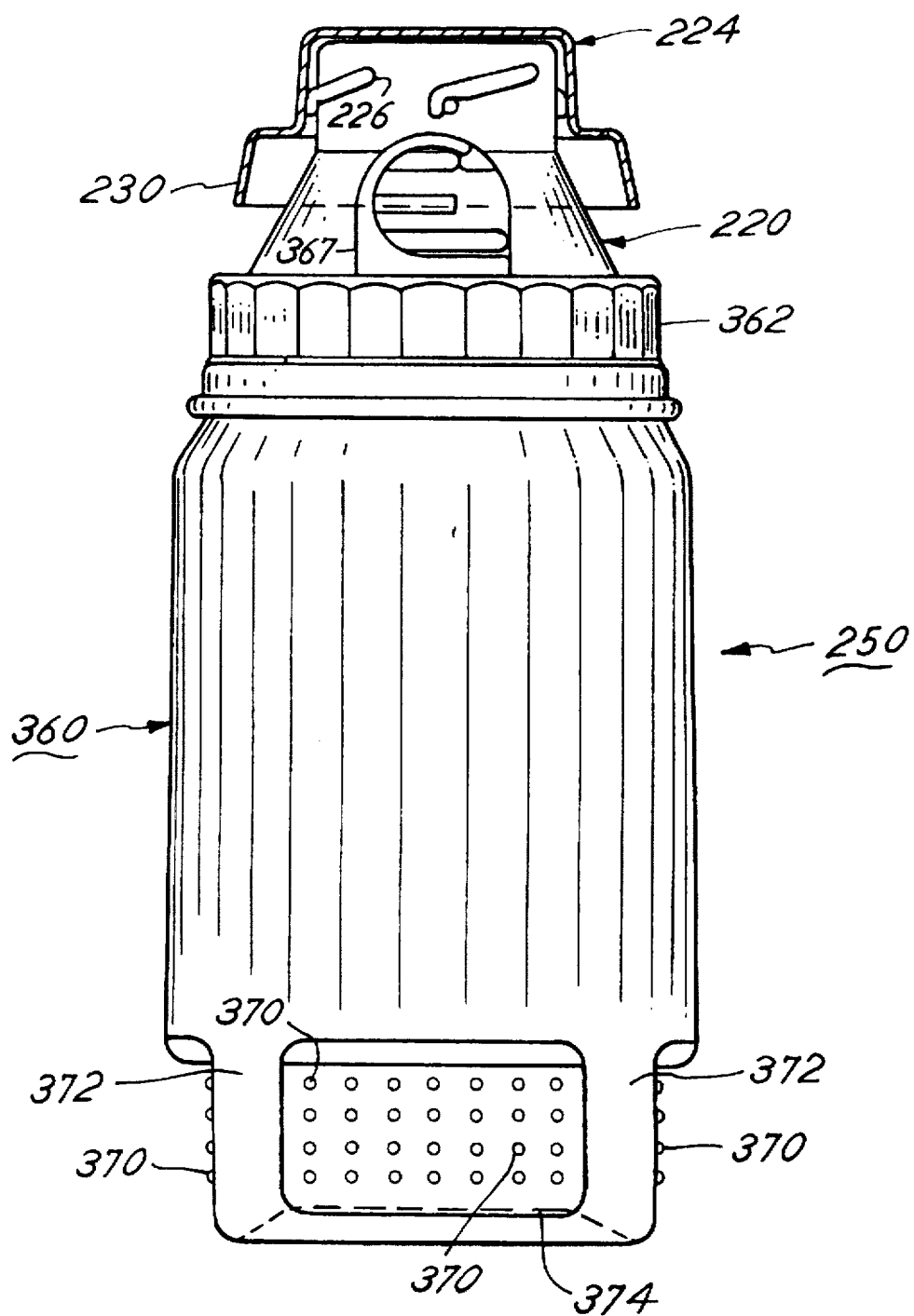

FIG. 14 is a plan view of the bottom of the bottle shell 360. The pairs of parallel sides provide gripping support when the vessel is screwed onto the opening apparatus 368. The bottom of the bottle shell has a concave surface 374 (see also FIG. 12) to reinforce the bottom against bulging. Reinforcing ribs or other structure can be used to assist in strengthening the bottom of the bottle against bulging due to exposure of the vessel to high temperatures, or pressure differentials between the interior of the bottle and the outside environment, as may be encountered at high elevations or if the bottles are shipped in airplanes.

Alternative embodiments for the gripping features 370 (see FIGS. 7, 12) at the bottom of the bottle shell 360 are illustrated in FIGS. 15A–15D.

The bottle shell 360 and cap 220 are preferably made from an inert, lightweight material that is capable of handling extremes of temperature without affecting the contents of the vessel. Presently preferred materials for both the cap and shell are high density polyethylene and polypropylene copolymer. The cap and shell need not be made from the same material. With either of these materials, a thickness for the shell of between 25 and 30 mils should be satisfactory for most applications. The thickness of the membrane may be varied depending on the opening structure that is used to open the vessel. Alternatively, if the vessels are opened by hand, well known opening structures can be used.

Persons of skill in the art will appreciate that considerable variation may be made from the illustrated embodiments without departure from the true spirit and scope of the invention. For example, the invention is applicable to other types of chemical vessel opening apparatus. Further, the chemicals may be used to contain other chemicals besides dialysate chemicals, such as chemicals for preparation of solutions used for surgical procedures. Other types of machine readable identifiers may be used besides touch memory buttons. The spirit and scope of the invention is defined in the appended claims, to be interpreted in light of the foregoing specification.

We claim:

1. A vessel mountable to an apparatus for opening said vessel, said vessel for containing a batch quantity of chemicals for preparation of physiologic, therapeutic, or irrigation fluids, comprising:

a bottle shell, a cap having a membrane having a first thickness for sealing said cap, said cap threadably engaging said bottle shell to cover said shell;

said membrane having a frangible section of a second thickness less than said first thickness for permitting said membrane to be opened by said apparatus for opening;

wherein said frangible membrane further comprises a peripheral portion, a hinge portion and a central portion, said hinge portion connecting said central portion of said frangible membrane to said exterior portion when said vessel is opened by said opening apparatus.

2. The vessel of claim 1, wherein said vessel further comprises a lower portion having two pairs of integral parallel sides to form a gripping structure for said vessel; and a concave surface formed in said lower portion between said two pairs of parallel sides to prevent said bottle shell from bulging.

3. The vessel as claimed in one of claim 1, wherein said vessel contains a batch quantity of dialysate chemicals.

4. A vessel mountable to an apparatus for opening said vessel, said apparatus for opening comprising a spike reciprocable between lower and upper positions, comprising:

a bottle having an interior portion, a bottom, a side wall and an upper portion, said upper portion forming an opening for said bottle, a frangible membrane sealing said opening;

a set of projecting thread elements applied to said upper portion of said bottle adjacent to said opening, said thread elements cooperating with corresponding groove elements on said mounting apparatus permitting said bottle to be securely and rotatably engaged onto said apparatus for opening said bottle in an upside-down condition such that said bottle and said membrane are positioned immediately above said opening apparatus;

said frangible membrane further comprising a peripheral portion, a central portion and a connecting portion linking said central portion of said membrane to said peripheral portion when said spike is moved to upper position to pierce said central portion of said membrane and open said vessel, whereby said central portion of said membrane remains attached to said bottle by said connecting portion upon opening of said bottle by said reciprocating spike; and a batch quantity of chemicals for preparation of a dialysate solution contained within said bottle.

5. The vessel of claim 4, wherein said membrane has a first thickness and wherein said central portion is circumscribed and separated from said peripheral portion of said membrane by a frangible section having a second thickness less than said first thickness.

6. The vessel of claim 4, further comprising a removable protective overcap engaging said projecting thread elements for protecting said frangible membrane during shipping.

7. The vessel of claim 1 or claim 4, wherein said frangible membrane is made from a polymeric material capable of withstanding exposure to water heated to a temperature of greater than 70 degrees C. for a period of at least one hour without affecting the composition of said chemicals stored within said bottle.

8. The vessel of claim 1 or claim 4, wherein said bottle further comprises an exterior surface and a machine-readable identifier affixed to the exterior surface of said bottle.

9. The vessel of claim 1 or claim 4, wherein said membrane further comprises a reinforcement of said central portion of said frangible membrane comprising an area of increased thickness of said membrane.

* * * * *

UNITED STATES PATENT AND TRADEMARK OFFICE
CERTIFICATE OF CORRECTION

PATENT NO.  : 5,788,099
DATED       : August 4, 1998
INVENTOR(S) : Dennis M. Treu et al It is certified that error appears in the above-identified patent and that said Letters Patent is hereby corrected as shown below:

On the title page: Item [73] Assignee should read -- AKSYS, LTD --.

Signed and Sealed this

Twenty-second Day of December, 1998

Attest:

BRUCE LEHMAN

Attesting Officer    Commissioner of Patents and Trademarks